US012558378B2

(12) United States Patent
Xu

(10) Patent No.: US 12,558,378 B2
(45) Date of Patent: *Feb. 24, 2026

(54) METHODS FOR LOWERING BLOOD GLUCOSE

(71) Applicant: Janssen Biotech, Inc., Horsham, PA (US)

(72) Inventor: Jean Xu, Skillman, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 618 days.

This patent is subject to a terminal disclaimer.

(21) Appl. No.: 17/830,739

(22) Filed: Jun. 2, 2022

(65) Prior Publication Data

US 2022/0296653 A1      Sep. 22, 2022

Related U.S. Application Data

(63) Continuation of application No. 16/539,401, filed on Aug. 13, 2019, now Pat. No. 11,369,642, which is a continuation of application No. 16/134,831, filed on Sep. 18, 2018, now Pat. No. 10,471,104, which is a continuation of application No. 12/838,998, filed on Jul. 19, 2010, now Pat. No. 10,076,544.

(60) Provisional application No. 61/226,923, filed on Jul. 20, 2009.

(51) Int. Cl.
*A61K 35/39*      (2015.01)

(52) U.S. Cl.
CPC .................................... *A61K 35/39* (2013.01)

(58) Field of Classification Search
CPC .................................................... A61K 35/39
See application file for complete search history.

(56) References Cited

U.S. PATENT DOCUMENTS

| | | | |
|---|---|---|---|
| 9,585,917 B2 | 3/2017 | Martinson et al. | |
| 10,076,544 B2 | 9/2018 | Xu | |
| 10,471,104 B2 | 11/2019 | Xu | |
| 2003/0138948 A1 | 7/2003 | Fisk et al. | |
| 2004/0121460 A1 | 6/2004 | Lumelsky et al. | |
| 2005/0054102 A1 | 3/2005 | Wobus et al. | |
| 2006/0281174 A1 | 12/2006 | Xu et al. | |
| 2007/0154981 A1 | 7/2007 | Hori et al. | |
| 2007/0259421 A1* | 11/2007 | D'Amour ................. A61P 3/10 435/366 |
| 2020/0030382 A1 | 1/2020 | Xu | |

FOREIGN PATENT DOCUMENTS

| | | |
|---|---|---|
| WO | WO 2002/092756 | 11/2002 |
| WO | 2003033697 A1 | 4/2003 |
| WO | WO 2003/029445 | 4/2003 |
| WO | 2004016747 A2 | 2/2004 |
| WO | WO 2004/011621 | 2/2004 |
| WO | 2004050872 A1 | 6/2004 |
| WO | WO 2004/050827 | 6/2004 |
| WO | 2007051038 A2 | 5/2007 |
| WO | 2007103282 A2 | 9/2007 |
| WO | WO 2007/103282 | 9/2007 |
| WO | WO 2007/127927 | 11/2007 |
| WO | WO 2008/013664 | 1/2008 |
| WO | WO 2009/012428 | 1/2009 |
| WO | 2006105152 A3 | 6/2009 |
| WO | 2009070592 A2 | 6/2009 |
| WO | WO 2009/070592 | 6/2009 |
| WO | WO 2009/090424 | 7/2009 |
| WO | WO 2010/051213 | 5/2010 |
| WO | WO 2010/051223 | 5/2010 |
| WO | WO 2011/079017 | 6/2011 |
| WO | WO 2011/081222 | 7/2011 |
| WO | WO 2011/160066 | 12/2011 |
| WO | WO 2013/095953 | 6/2013 |
| WO | 2014105543 A1 | 7/2014 |

OTHER PUBLICATIONS

Lin et al. (2009, Transplant Immunology, vol. 21, pp. 75-80) (Year: 2009).*
Ekser et al. (Oct. 21, 2011, the Lancet, pp. 1-12) (Year: 2011).*
Narang et al., 2006, Pharmacological Reviews, vol. 58(2), pp. 194-243 (Year: 2006).*
Agulnick et al., "Insulin-Producing Endocrine Cells Differentiated In Vitro from Human Embryonic Stem Cells Function in Macroencapsulation Devices In Vivo", *Stem Cells Transl. Med.*, vol. 4:1-9, 2015.
Best et al., "Embryonic Stem Cells to Beta-Cells by Understanding Pancreas Development," *Mol. Cell. Endocrinol.*, vol. 288:86-94, 2008.
Bose et al., Human Embryonic Stem Cell Differentiation into Insulin Secreting β-cells for Diabetes, *Cell Biol. Int.*, vol. 36:1013-1020, 2012.
D'Amour et al., "Production of pancreatic hormone-expressing endocrine cells from human embryonic stem cells," *Nat. Biotechnol.*, vol. 24:1392-1401, 2006.
Fryer et al., "Generating β-cells in vitro: progress towards a Holy Grail," *Curr. Opin. Endocrinol. Diabetes Obes.*, vol. 20:112-117, 2013.
Guo et al., "Stem Cells to Pancreatic β-Cells: New Sources for Diabetes Cell Therapy," *Endocr. Rev.*, vol. 30:214-227, 2009.
Harmon et al., "GDF11 Modulates NGN3+ Islet Progenitor Cell Number and Promotes β-Cell Differentiation in Pancreas Development," *Development*, vol. 131:6163-6174, 2004.
Hosoya et al., "Induction of Differentiation of Undifferentiated Cells into Pancreatic Beta-Cells in Vertebrates," *Int. J. Dev. Biol.*, vol. 56:313-323, 2012.
Jennings et al., "Development of the Human Pancreas from Foregut to Endocrine Commitment," *Diabetes*, vol. 62:3514-3522, 2013.

(Continued)

Primary Examiner — Anoop K Singh
Assistant Examiner — David A Montanari
(74) Attorney, Agent, or Firm — Klarquist Sparkman, LLP

(57) ABSTRACT

The present invention provides a method for lowering blood glucose levels in an animal by transplanting a population of pancreatic endocrine precursor cells into an animal.

3 Claims, 22 Drawing Sheets

(56) References Cited

OTHER PUBLICATIONS

Jiang et al., "Generation of Insulin-Producing Islet-Like Clusters from Human Embryonic Stem Cells," *Stem Cells*, vol. 25:1940-1953, 2007.

Jiang et al., "In Vitro Derivation of Functional Insulin-Producing Cells from Human Embryonic Stem Cells," *Cell Res.*, vol. 17:333-344, 2007.

Kieffer et al., "Beta-Cell Replacement Strategies for Diabetes," *J. Diabetes Investig.*, vol. 9:457-463, 2018.

Kumar et al., "Recent Developments in β-Cell Differentiation of Pluripotent Stem Cells Induced by Small and Large Molecules, *Int. J. Mol. Sci.*," vol. 15:23418-23447, 2014.

Lee et al., "Human β-cell Precursors Mature into Functional Insulin-producing Cells in an Immunoisolation Device: Implications for Diabetes Cell Therapies," *Transplant.*, vol. 87:983-991, 2009.

Nostro et al., "Generation of Beta Cells from Human Pluripotent Stem Cells: Potential for Regenerative Medicine," *Semin. Cell Dev. Biol.*, vol. 23:701-710, 2012.

Pagliuca et al., "How to Make a Functional β-Cell," *Development*, vol. 140:2472-2483, 2013.

Rezania et al., "Production of Functional Glucagon-Secreting β-Cells from Human Embryonic Stem Cells," *Diabetes*, vol. 60:239-247, 2011.

Segev et al., "Differentiation of Human Embryonic Stem Cells into Insulin-Producing Clusters," *Stem Cells*, vol. 22:265-274, 2004.

Shim et al., "Directed Differentiation of Human Embryonic Stem Cells Towards a Pancreatic Cell Fate," *Diabetologia*, vol. 50:1228-1238, 2007.

Shiraki et al., "Guided Differentiation of Embryonic Stem Cells into Pdx1-Expressing Regional-Specific Definitive Endoderm," *Stem Cells*, vol. 26: 874-885, 2008.

Soria et al., "From Stem Cells to Beta Cells: New Strategies in Cell Therapy of Diabetes Mellitus," *Diabetologia*, vol. 44:407-415, 2001.

Spence et al., "Translational Embryology: Using Embryonic Principles to Generate Pancreatic Endocrine Cells from Embryonic Stem Cells," *Dev. Dyn.*, vol. 236:3218-3227, 2007.

Wei et al., "Cdk5-dependent Regulation of Glucose-Stimulated Insulin Secretion," *Nature Med.*, vol. 11:1104-1108, 2005.

Xudong et al., "Research Progress in Inducing Stem Cells to Differentiate toward the B-like Cells of Pancreatic Islet," *Chinese Bulletin of Life Sciences*, vol. 19:526-530, 2007.

Zhang et al., "Highly Efficient Differentiation of Human ES Cells and iPS Cells into Mature Pancreatic Insulin-Producing Cells," *Cell Res.*, vol. 19:429-438, 2009.

Zhang et al., "MafA Is a Key Regulator of Glucose-Stimulated Insulin Secretion," *Mol. Cell. Biol.*, vol. 25:4969-4976, 2005.

Zhao et al., "The Islet β Cell-enriched MafA Activator is a Key Regulator of Insulin Gene Transcription," *J. Biol. Chem.*, vol. 280:11887-11894, 2005.

Altirriba, et al. "The Role of Transmembrane Protein 27 (TMEM27) in islet physiology and its potential use as a beta cell mass biomarker." Diabetologia (2010): 53: 1406-1414.

Banerjee and Otonkoski, "A simple two-step protocol for the purification of human pancreatic beta cells." Diabetologia (2009) 52: 621-625.

Brewer, et al. "Optimized Survivial of Hippocampal Neurons in B27-Supplemented Neurobasal, a New Serum-free Medium Combination." Journal of Neuroscience Research 35: 567-576 (1993).

Cho, et al. "Inhibition of Activin/Nodal Signalling is necessary for pancreatic differentiatoin of human pluripotent stem cells." Diabetologia (2012) 55: 3284-3295.

Cuny, et al. Structure-activity relationship study of bone morphogenetic protein (BMP) signaling inhibitors. Bioorg Med Chem Lett. Aug. 1, 2008; 18(15): 4388-4392.

Fraker, et al. "Enhanced Oxygenation Promotes B-Cell Differentiation in Vitro." Stem Cells 2007; 25: 3155-3164.

Hald, et al."Pancreatic Islet and Progenitor Cell Surface Markers with Cell Sorting Potential". Diabetologia (2012) 55: 154-165.

Hussain, et al., Stem-Cell Therapy for Diabetes Mellitus, Lancet, 2004, pp. 203-205, vol. 364.

Iype, et al. "The Transcriptional Repressor Nkx6.1 Also Functions as Deoxyribonucleic Acid Context-Dependent Transcriptional Activator During Pancreatic B-cell Differentiation: Evidence for Feedback Activation of the nkx6.1 Gene by Nkx6.1" Molecular Endocrinology 18(6): 1363-1375.

Kahan, Pancreatic Precursors and Differentiated Islet Cell Types from Murine Embryonic Stem Cells, Diabetes, Aug. 2003, pp. 2016-2042, vol. 52.

Korytnikov, et al. "Generation of Polyhormonal and Multipotent pancreatic progenitor lineages from human pluripotent stem cells." Methods, vol. 101, May 15, 2016, pp. 56-64.

Leontovyc, et al. The Effect of Epigenetic Factors on Differentiation of Pancreatic Progenitor Cells into Insulin-Producing Cells. Transplant. Proc. 2011, vol. 43, pp. 3212-3216.

Mfopou, et al. "Noggin, Retinoids, and Fibroblast Growth Factor Regulates Hepatic or Pancreatic Fate of Human Embryonic Stem Cells." Gastroenterology 2010; 138:2233-2245.

Micallef, et al. "INSGFP/W Human Embryonic Stem Cells Facilitate Isolation of in vitro derived insulin-producing cells." Diabetologia (2012) 55: 694-706.

Stassi, et al. "Expression of Apotosis-Inducing CD95 (Fas/Apo-1) on Human B-Cells Sorted by Flow-Cytometry and Cultured in Vitro." Transplantation Proceedings, vol. 27, No. 6 (December), 1995: 3271-3275.

* cited by examiner

NKX6.1 (Stage 4, Day 3)

PTF1a (Stage 4, Day 3)

Ngn3 (Stage 4, Day 3)

FIG. 5A

PCR Analysis (Stage 4)

FIG. 5B

Insulin Expression

FIG. 6

H1S4 Recipient C-peptide

FIG. 12A
FIG. 12B
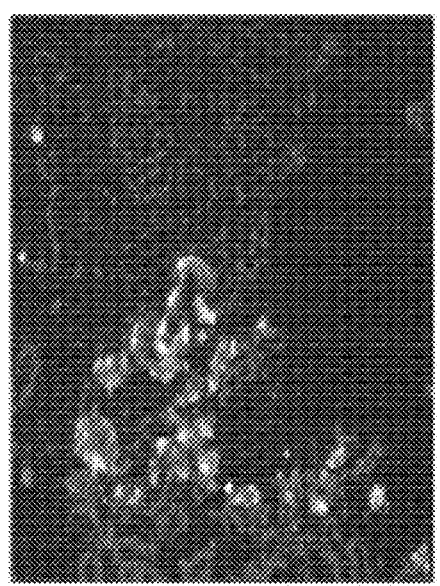
FIG. 12C
FIG. 12D
FIG. 12E
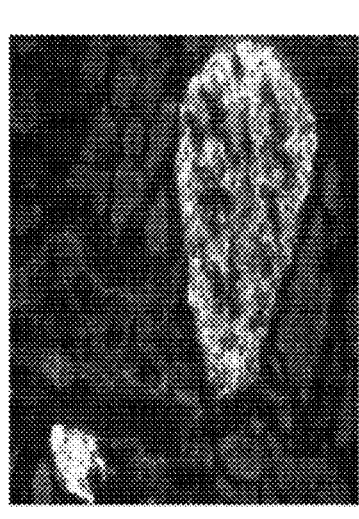
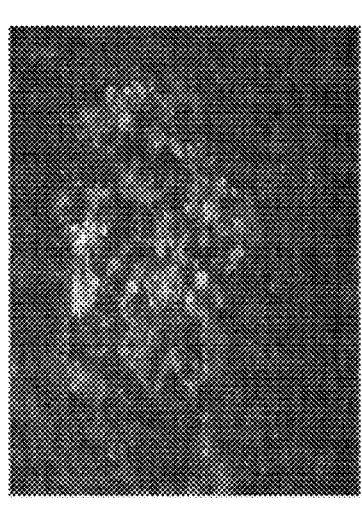

METHODS FOR LOWERING BLOOD GLUCOSE

CROSS REFERENCE TO RELATED APPLICATIONS

The application is a continuation of U.S. patent application Ser. No. 16/539,401, filed Aug. 13, 2019, issued as U.S. Pat. No. 11,369,642 on Jun. 28, 2022, which is a continuation of U.S. patent application Ser. No. 16/134,831, filed Sep. 18, 2018, issued as U.S. Pat. No. 10,471,104 on Nov. 12, 2019, which is a continuation of U.S. patent application Ser. No. 12/838,998, filed Jul. 19, 2010, issued as U.S. Pat. No. 10,076,544 on Sep. 18, 2018, which claims priority to U.S. Provisional Patent Application No. 61/226,923, filed Jul. 20, 2009. The above-listed applications are herein incorporated by reference in their entirety.

FIELD OF THE INVENTION

The present invention provides a method for lowering blood glucose levels in an animal by transplanting a population of pancreatic endocrine precursor cells into an animal.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent stem cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, for example, HNF3 beta, GATA4, MIXL1, CXCR4 and SOX17.

Formation of the pancreas arises from the differentiation of definitive endoderm into pancreatic endoderm. Cells of the pancreatic endoderm express the pancreatic-duodenal homeobox gene, PDX1. In the absence of PDX1, the pancreas fails to develop beyond the formation of ventral and dorsal buds. Thus, PDX1 expression marks a critical step in pancreatic organogenesis. The mature pancreas contains, among other cell types, exocrine tissue and endocrine tissue. Exocrine and endocrine tissues arise from the differentiation of pancreatic endoderm.

Cells bearing the features of islet cells have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

In one example, Hori et al. (PNAS 99: 16105, 2002) disclose that treatment of mouse embryonic stem cells with inhibitors of phosphoinositide 3-kinase (LY294002) produced cells that resembled β cells.

In another example, Blyszczuk et al. (PNAS 100:998, 2003) reports the generation of insulin-producing cells from mouse embryonic stem cells constitutively expressing Pax4.

Micallef et al. reports that retinoic acid can regulate the commitment of embryonic stem cells to form PDX1 positive pancreatic endoderm. Retinoic acid is most effective at inducing PDX1 expression when added to cultures at day four of embryonic stem cell differentiation during a period corresponding to the end of gastrulation in the embryo (Diabetes 54:301, 2005).

Miyazaki et al. reports a mouse embryonic stem cell line over-expressing Pdx1. Their results show that exogenous Pdx1 expression clearly enhanced the expression of insulin, somatostatin, glucokinase, neurogenin3, p48, Pax6, and HNF6 genes in the resulting differentiated cells (Diabetes 53: 1030, 2004).

Skoudy et al. reports that activin A (a member of the TGF-β superfamily) upregulates the expression of exocrine pancreatic genes (p48 and amylase) and endocrine genes (Pdx1, insulin, and glucagon) in mouse embryonic stem cells. The maximal effect was observed using 1 nM activin A. They also observed that the expression level of insulin and Pdx1 mRNA was not affected by retinoic acid; however, 3 nM FGF7 treatment resulted in an increased level of the transcript for Pdx1 (Biochem. J. 379: 749, 2004).

Shiraki et al. studied the effects of growth factors that specifically enhance differentiation of embryonic stem cells into PDX1 positive cells. They observed that TGF-β2 reproducibly yielded a higher proportion of PDX1 positive cells (Genes Cells. 2005 June; 10(6): 503-16).

Gordon et al. demonstrated the induction of brachyury [positive]/HNF3 beta [positive] endoderm cells from mouse embryonic stem cells in the absence of serum and in the presence of activin along with an inhibitor of Wnt signaling (US 2006/0003446A1).

Gordon et al. (PNAS, Vol 103, page 16806, 2006) states "Wnt and TGF-beta/nodal/activin signaling simultaneously were required for the generation of the anterior primitive streak".

However, the mouse model of embryonic stem cell development may not exactly mimic the developmental program in higher mammals, such as, for example, humans.

Thomson et al. isolated embryonic stem cells from human blastocysts (Science 282:114, 1998). Concurrently, Gearhart and coworkers derived human embryonic germ (hEG) cell lines from fetal gonadal tissue (Shamblott et al., Proc. Natl. Acad. Sci. USA 95:13726, 1998). Unlike mouse embryonic stem cells, which can be prevented from differentiating simply by culturing with Leukemia Inhibitory Factor (LIF), human embryonic stem cells must be maintained under very special conditions (U.S. Pat. No. 6,200,806; WO 99/20741; WO 01/51616).

D'Amour et al. describes the production of enriched cultures of human embryonic stem cell-derived definitive endoderm in the presence of a high concentration of activin and low serum (Nature Biotechnology 2005). Transplanting these cells under the kidney capsule of mice resulted in differentiation into more mature cells with characteristics of some endodermal organs. Human embryonic stem cell-derived definitive endoderm cells can be further differentiated into PDX1 positive cells after addition of FGF-10 (US 2005/0266554A1).

D'Amour et al. (Nature Biotechnology—24, 1392-1401 (2006)) states: "We have developed a differentiation process that converts human embryonic stem (hES) cells to endocrine cells capable of synthesizing the pancreatic hormones insulin, glucagon, somatostatin, pancreatic polypeptide and ghrelin. This process mimics in vivo pancreatic organogenesis by directing cells through stages resembling definitive endoderm, gut-tube endoderm, pancreatic endoderm and endocrine precursor en route to cells that express endocrine hormones".

In another example, Fisk et al. reports a system for producing pancreatic islet cells from human embryonic stem cells (US2006/0040387A1). In this case, the differentiation pathway was divided into three stages. Human embryonic stem cells were first differentiated to endoderm using a combination of sodium butyrate and activin A. The cells were then cultured with TGF-β antagonists such as Noggin in combination with EGF or betacellulin to generate PDX1 positive cells. The terminal differentiation was induced by nicotinamide.

In one example, Benvenistry et al. states: "We conclude that over-expression of PDX1 enhanced expression of pancreatic enriched genes, induction of insulin expression may require additional signals that are only present in vivo" (Benvenistry et al., Stem Cells 2006; 24:1923-1930).

In another example, US2008/0241107A1 claims a method for producing a cell that secretes insulin comprising: a) obtaining a cell that does not produce insulin; and, b) incubating the cell with media containing high glucose, wherein the cell secretes insulin.

Therefore, there still remains a significant need to develop conditions for establishing pluripotent stem cell lines that can be expanded to address the current clinical needs, while retaining the potential to differentiate into pancreatic endocrine cells, pancreatic hormone expressing cells, or pancreatic hormone secreting cells. We have taken an alternative approach to improve the efficiency of differentiating human embryonic stem cells toward pancreatic endocrine cells.

SUMMARY

In one embodiment, the present invention provides a method for lowering blood glucose levels in an animal by transplanting a population of pancreatic endocrine precursor cells into an animal.

BRIEF DESCRIPTION OF THE DRAWINGS

FIG. 5A shows the expression of PDX1, NKX6.1, NGN, and PTF1 alpha in cells treated according to the methods described in Example 3. Duplicate samples were collected for real-time PCR analysis at stage 4 day 3. The plots represent fold induction for each gene relative to the expression of genes of Treatment group one at stage 4 day 3. The light grey bars represent data from samples taken from cells harvested from the T1 (treatment 1) group. The white bars represent data from samples taken from cells harvested from the T2 (treatment 2) group. The dark grey bars represent data from samples taken from cells harvested from the T3 (treatment 3) group. The black bars represent data from samples taken from cells harvested from the T4 (treatment 4) group. FIG. 5B shows the expression of insulin in cells treated according to the methods described in Example 3. Duplicate samples were collected for real-time PCR analysis at stage 4 day 3 (S4, D3), and at stage 4, day 8 (S4, D8). The plots represent fold induction for each gene relative to the expression of genes of Treatment group one (T1) at stage 4 day 3.

FIG. 6 shows glucose stimulated human C-peptide release kinetics of transplanted endocrine precursor cells. Specifically shown are the levels of human C-peptide (y-axis) 60 minutes after glucose administration. The x-axis indicates the animal number and days post-transplant.

(FIG. 11A) Micrographs from serial sections staining for human nuclear antigen and DAPI; (FIG. 11B) staining for CK19 and PDX1.

FIGS. 12A-12E show the morphological and immunofluorescence analysis of graft samples stained for insulin and glucagon at 3 weeks (FIG. 12A), 10 weeks (FIG. 12B) and 13 weeks (FIG. 12C) post implant. FIG. 12D shows the morphological and immunofluorescence analysis of graft samples stained for PDX1 and insulin at 13 weeks post implant. FIG. 12E shows the morphological and immunofluorescence analysis of graft samples stained for NEU-ROD1 and insulin at 13 weeks post implant.

DETAILED DESCRIPTION

Figure 1A:
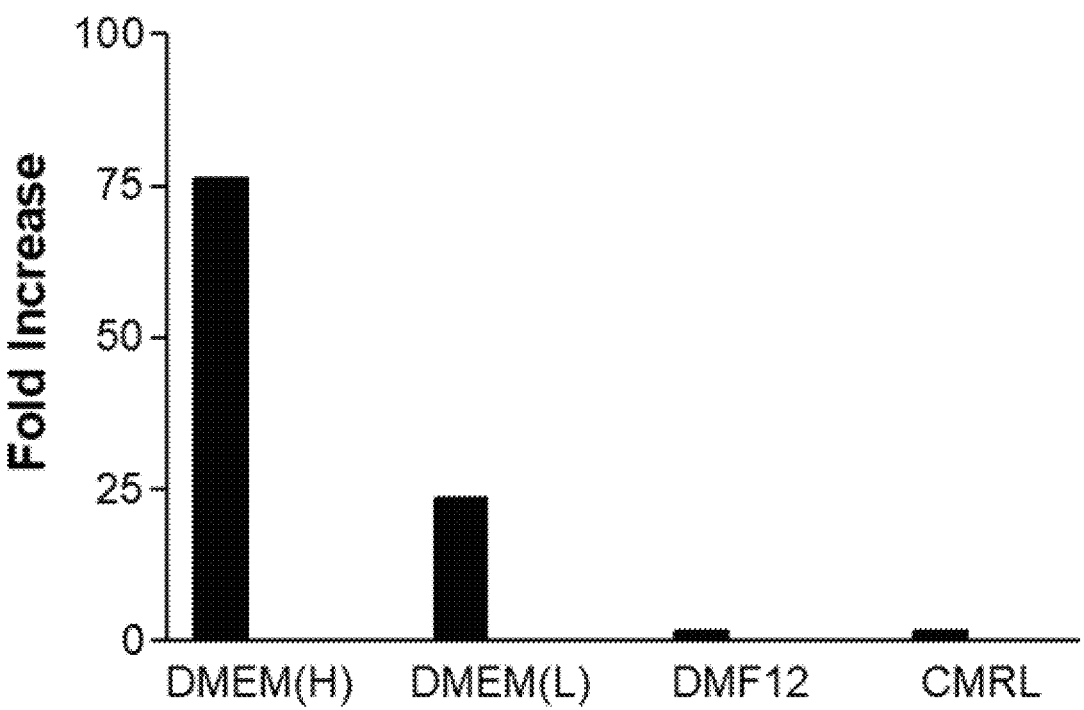
FIGS. 1A-1D show the effect of different basal media on the expression of NKX6.1 (FIG. 1A), PDX1 (FIG. 1B), PTF1 alpha (FIG. 1C) and NGN3 (FIG. 1D). Duplicate samples were collected at stage 4, day 3 for real-time PCR analysis. The plots represent fold induction for each gene relative to the DMEM/F12.
Figure 1B:
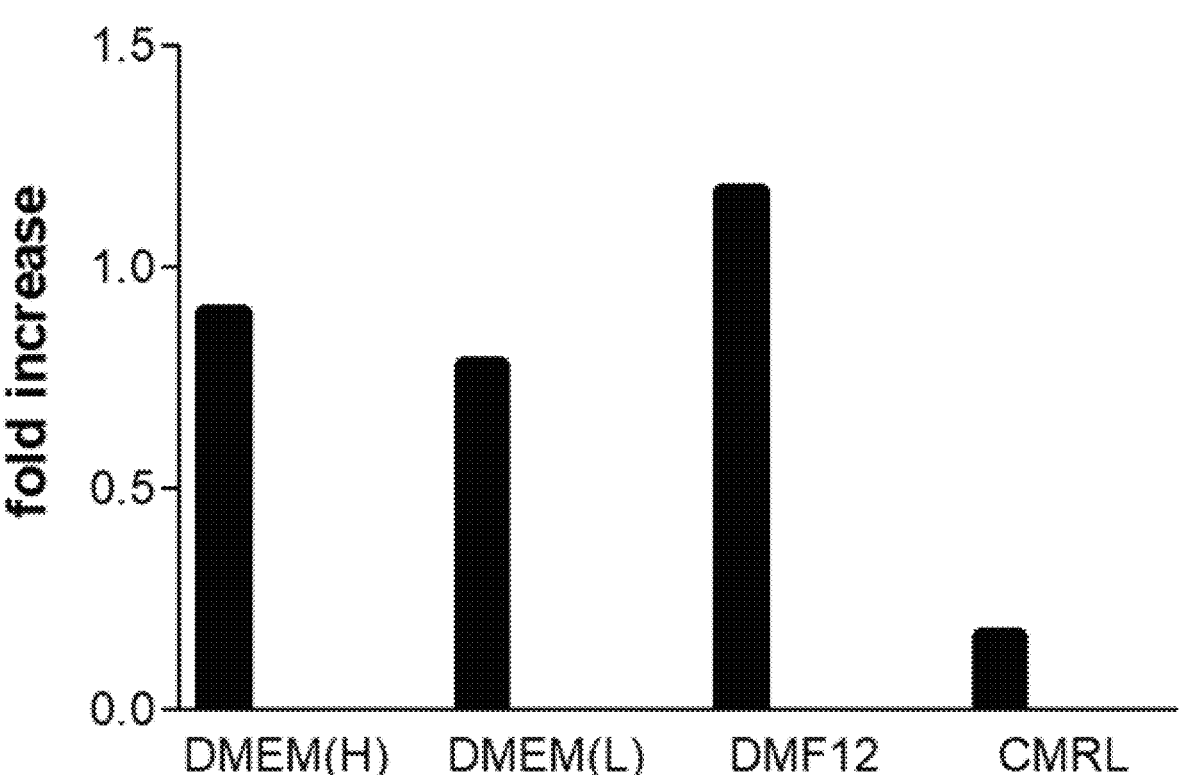
Figure 1C:
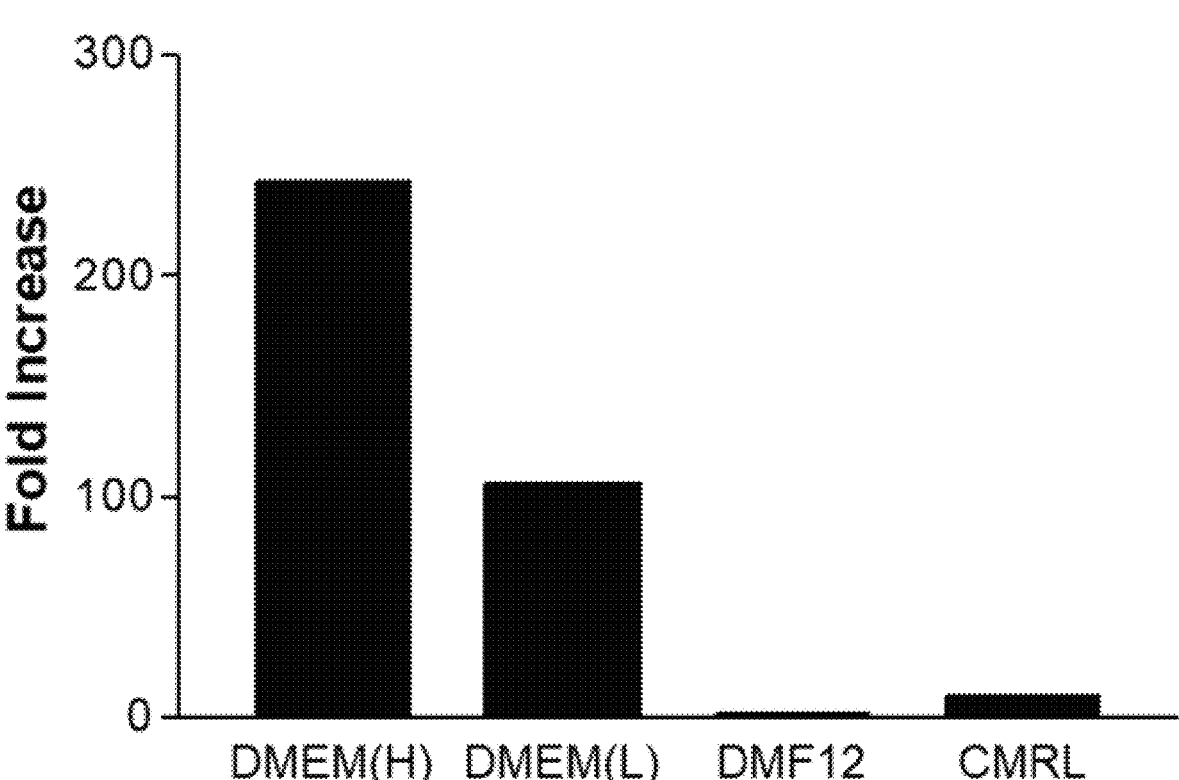
Figure 1D:
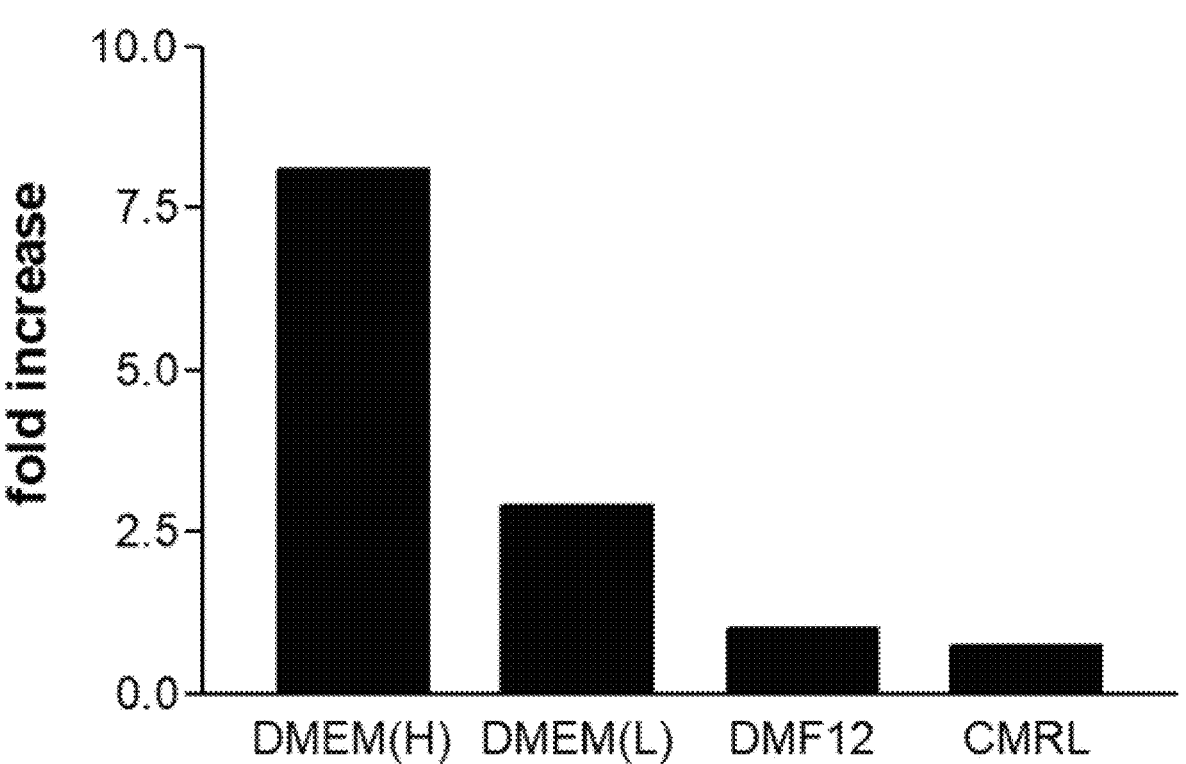

For clarity of disclosure, and not by way of limitation, the detailed description of the invention is divided into the following subsections that describe or illustrate certain features, embodiments or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Cells expressing markers characteristic of the definitive endoderm lineage", or "Stage 1 cells", or "Stage 1", as used herein, refers to cells expressing at least one of the following markers: SOX-17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage", as used herein, refers to cells expressing at least one of the following markers: PDX1, HNF-1 beta, PTF1 alpha, HNF6, or HB9. Cells expressing markers characteristic of the pancreatic endoderm lineage include pancreatic endoderm cells, primitive gut tube cells, and posterior foregut cells.

"Cells expressing markers characteristic of the pancreatic endocrine lineage", as used herein, refers to cells expressing at least one of the following markers: NEUROD, ISL1, PDX1, NKX6.1, MAFB, insulin, glucagon, or somatostatin. Cells expressing markers characteristic of the pancreatic endocrine lineage include pancreatic endocrine cells, pancreatic hormone expressing cells, and pancreatic hormone secreting cells, and cells of the R-cell lineage.

"Definitive endoderm", as used herein, refers to cells which bear the characteristics of cells arising from the epiblast during gastrulation and which form the gastrointestinal tract and its derivatives. Definitive endoderm cells express the following markers: HNF3 beta, GATA4, SOX17, Cerberus, OTX2, goosecoid, C-Kit, CD99, and MIXL1.

"Markers", as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Pancreatic endocrine cell", or "pancreatic hormone expressing cell", as used herein, refers to a cell capable of expressing at least one of the following hormones: insulin, glucagon, somatostatin, and pancreatic polypeptide.

"Pancreatic endocrine precursor cell", as used herein refers to a multipotent cell of the definitive endoderm lineage that expresses NGN3 and which can further differentiate into cells of the endocrine system including, but not limited to, pancreatic islet hormone-expressing cells. Endocrine precursor cells cannot differentiate into as many different cell, tissue and/or organ types as compared to less specifically differentiated definitive endoderm lineage cells, such as PDX1 positive pancreatic endoderm cells.

"Pancreatic hormone producing cell", as used herein, refers to a cell capable of producing at least one of the following hormones: insulin, glucagon, somatostatin, and pancreatic polypeptide.

"Pancreatic hormone secreting cell" as used herein, refers to a cell capable of secreting at least one of the following hormones: insulin, glucagon, somatostatin, and pancreatic polypeptide.

Isolation, Expansion and Culture of Pluripotent Stem Cells Characterization of Pluripotent Stem Cells Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, GA).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Pluripotent Stem Cells

In one embodiment, pluripotent stem cells are typically cultured on a layer of feeder cells that support the pluripotent stem cells in various ways. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is supported using a medium conditioned by culturing previously with another cell type. Alternatively, the growth of pluripotent stem cells in feeder-free culture without differentiation is supported using a chemically defined medium.

For example, Reubinoff et al. (Nature Biotechnology 18: 399-404 (2000)) and Thompson et al. (Science 6 Nov. 1998: Vol. 282. no. 5391, pp. 1145-1147) disclose the culture of pluripotent stem cell lines from human blastocysts using a mouse embryonic fibroblast feeder cell layer.

Richards et al., (Stem Cells 21: 546-556, 2003) evaluated a panel of eleven different human adult, fetal and neonatal feeder cell layers for their ability to support human pluripotent stem cell culture. Richards et al., states: "human embryonic stem cell lines cultured on adult skin fibroblast feeders retain human embryonic stem cell morphology and remain pluripotent".

US20020072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. US20020072117 also discloses the use of the cell lines as a primary feeder cell layer.

In another example, Wang et al (Stem Cells 23: 1221-1227, 2005) discloses methods for the long-term growth of human pluripotent stem cells on feeder cell layers derived from human embryonic stem cells.

In another example, Stojkovic et al (Stem Cells 2005 23: 306-314, 2005) disclose a feeder cell system derived from the spontaneous differentiation of human embryonic stem cells.

In a further example, Miyamoto et al (Stem Cells 22: 433-440, 2004) disclose a source of feeder cells obtained from human placenta.

Amit et al (Biol. Reprod 68: 2150-2156, 2003) discloses a feeder cell layer derived from human foreskin.

In another example, Inzunza et al (Stem Cells 23: 544-549, 2005) disclose a feeder cell layer from human postnatal foreskin fibroblasts.

U.S. Pat. No. 6,642,048 discloses media that support the growth of primate pluripotent stem (pPS) cells in feeder-free culture, and cell lines useful for production of such media. U.S. Pat. No. 6,642,048 states: "This invention includes mesenchymal and fibroblast-like cell lines obtained from embryonic tissue or differentiated from embryonic stem cells. Methods for deriving such cell lines, processing media, and growing stem cells using the conditioned media are described and illustrated in this disclosure."

In another example, WO2005014799 discloses conditioned medium for the maintenance, proliferation and differentiation of mammalian cells. WO2005014799 states: "The culture medium produced in accordance with the present invention is conditioned by the cell secretion activity of murine cells; in particular, those differentiated and immortalized transgenic hepatocytes, named MMH (Met Murine Hepatocyte)."

In another example, Xu et al (Stem Cells 22: 972-980, 2004) discloses conditioned medium obtained from human embryonic stem cell derivatives that have been genetically modified to over express human telomerase reverse transcriptase.

In another example, US20070010011 discloses a chemically defined culture medium for the maintenance of pluripotent stem cells.

An alternative culture system employs serum-free medium supplemented with growth factors capable of promoting the proliferation of embryonic stem cells. For example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, Levenstein et al (Stem Cells 24: 568-574, 2006) disclose methods for the long-term culture of human embryonic stem cells in the absence of fibroblasts or conditioned medium, using media supplemented with bFGF.

In another example, US20050148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, U.S. Pat. No. 6,800,480 states "In one embodiment, a cell culture medium for growing primate-derived primordial stem cells in a substantially undifferentiated state is provided which includes a low osmotic pressure, low endotoxin basic medium that is effective to support the growth of primate-derived primordial stem cells. The basic medium is combined with a nutrient serum effective to support the growth of primate-derived primordial stem cells and a substrate selected from the group consisting of feeder cells and an extracellular matrix component derived from feeder cells. The medium further includes non-essential amino acids, an anti-oxidant, and a first growth factor selected from the group consisting of nucleosides and a pyruvate salt."

In another example, US20050244962 states: "In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor."

In a further example, WO2005065354 discloses a defined, isotonic culture medium that is essentially feeder-free and serum-free, comprising: a. a basal medium; b. an amount of bFGF sufficient to support growth of substantially undifferentiated mammalian stem cells; c. an amount of insulin sufficient to support growth of substantially undifferentiated mammalian stem cells; and d. an amount of ascorbic acid sufficient to support growth of substantially undifferentiated mammalian stem cells.

In another example, WO2005086845 discloses a method for maintenance of an undifferentiated stem cell, said method comprising exposing a stem cell to a member of the transforming growth factor-beta (TGF-β) family of proteins, a member of the fibroblast growth factor (FGF) family of proteins, or nicotinamide (NIC) in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as, for example, those derived from basement membrane or that may form part of adhesion molecule receptor-ligand couplings. In one embodiment, the suitable culture substrate is MATRIGEL® (Becton Dickenson). MATRIGEL® is a soluble preparation from Engelbreth-Holm Swarm tumor cells that gels at room temperature to form a reconstituted basement membrane.

Other extracellular matrix components and component mixtures are suitable as an alternative. Depending on the cell type being proliferated, this may include laminin, fibronectin, proteoglycan, entactin, heparan sulfate, and the like, alone or in various combinations.

The pluripotent stem cells may be plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Suitable culture media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Formation of Pancreatic Endocrine Precursor Cells

In one embodiment, the present invention provides a method for producing pancreatic endocrine precursor cells, comprising the steps of:

a. Culturing pluripotent stem cells, b. Differentiating the pluripotent stem cells into cells expressing markers characteristic of the definitive endoderm lineage, c. Differentiating the cells expressing markers characteristic of the definitive endoderm lineage into cells expressing markers characteristic of the pancreatic endoderm lineage, and d. Differentiating the cells expressing markers characteristic of the pancreatic endoderm lineage into pancreatic endocrine precursor cells.

Pluripotent stem cells suitable for use in the present invention include, for example, the human embryonic stem cell line H9 (NIH code: WA09), the human embryonic stem cell line H1 (NIH code: WA01), the human embryonic stem cell line H7 (NIH code: WA07), and the human embryonic stem cell line SA002 (Cellartis, Sweden). Also suitable for use in the present invention are cells that express at least one of the following markers characteristic of pluripotent cells: ABCG2, CRIPTO, CD9, FOXD3, Connexin43, Connexin45, OCT4, SOX2, Nanog, hTERT, UTF1, ZFP42, SSEA-3, SSEA-4, Tra 1-60, Tra 1-81.

Markers characteristic of the definitive endoderm lineage are selected from the group consisting of SOX17, GATA4, HNF3 beta, GSC, CER1, Nodal, FGF8, Brachyury, Mix-like homeobox protein, FGF4 CD48, eomesodermin (EOMES), DKK4, FGF17, GATA6, CXCR4, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endoderm lineage are selected from the group consisting of PDX1, HNF1 beta, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of pancreatic endocrine precursor cells are selected from the group consisting of NGN3, NKX6.1, NeuroD, ISL1, PDX1, PAX4, NKX2.2, or ARX. Suitable for use in the present invention is a cell that expresses at least one of the markers characteristic of pancreatic endocrine precursor cells.

Formation of Cells Expressing Markers Characteristic of the Definitive Endoderm Lineage Pluripotent stem cells may be differentiated into cells expressing markers characteristic of the definitive endoderm lineage by any method in the art or by any method proposed in this invention.

For example, pluripotent stem cells may be differentiated into cells expressing markers characteristic of the definitive endoderm lineage according to the methods disclosed in D'Amour et al., Nature Biotechnology 23, 1534-1541 (2005).

For example, pluripotent stem cells may be differentiated into cells expressing markers characteristic of the definitive endoderm lineage according to the methods disclosed in Shinozaki et al., Development 131, 1651-1662 (2004).

For example, pluripotent stem cells may be differentiated into cells expressing markers characteristic of the definitive endoderm lineage according to the methods disclosed in McLean et al., Stem Cells 25, 29-38 (2007).

For example, pluripotent stem cells may be differentiated into cells expressing markers characteristic of the definitive endoderm lineage according to the methods disclosed in D'Amour et al., Nature Biotechnology 24, 1392-1401 (2006).

For example, pluripotent stem cells may be differentiated into cells expressing markers characteristic of the definitive endoderm lineage by culturing the pluripotent stem cells in medium containing activin A in the absence of serum, then culturing the cells with activin A and serum, and then culturing the cells with activin A and serum of a different concentration. An example of this method is disclosed in Nature Biotechnology 23, 1534-1541 (2005).

For example, pluripotent stem cells may be differentiated into cells expressing markers characteristic of the definitive endoderm lineage by culturing the pluripotent stem cells in medium containing activin A in the absence of serum, then culturing the cells with activin A with serum of another concentration. An example of this method is disclosed in D'Amour et al., Nature Biotechnology, 2005.

For example, pluripotent stem cells may be differentiated into cells expressing markers characteristic of the definitive endoderm lineage by culturing the pluripotent stem cells in medium containing activin A and a Wnt ligand in the absence of serum, then removing the Wnt ligand and culturing the cells with activin A with serum. An example of this method is disclosed in Nature Biotechnology 24, 1392-1401 (2006).

For example, pluripotent stem cells may be differentiated into cells expressing markers characteristic of the definitive endoderm lineage by treating the pluripotent stem cells according to the methods disclosed in U.S. patent application Ser. No. 11/736,908, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 11/779,311, assigned to LifeScan, Inc.

For example, pluripotent stem cells may be differentiated into cells expressing markers characteristic of the definitive endoderm lineage by treating the pluripotent stem cells according to the methods disclosed in U.S. patent application Ser. No. 60/990,529.

For example, pluripotent stem cells may be differentiated into cells expressing markers characteristic of the definitive endoderm lineage by treating the pluripotent stem cells according to the methods disclosed in U.S. patent application Ser. No. 61/076,889.

For example, pluripotent stem cells may be differentiated into cells expressing markers characteristic of the definitive endoderm lineage by treating the pluripotent stem cells according to the methods disclosed in U.S. patent application Ser. No. 61/076,900.

For example, pluripotent stem cells may be differentiated into cells expressing markers characteristic of the definitive endoderm lineage by treating the pluripotent stem cells according to the methods disclosed in U.S. patent application Ser. No. 61/076,908.

For example, pluripotent stem cells may be differentiated into cells expressing markers characteristic of the definitive endoderm lineage by treating the pluripotent stem cells according to the methods disclosed in U.S. patent application Ser. No. 61/076,915.

Characterization of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998))

Characteristics of pluripotent stem cells are well known to those skilled in the art, and additional characteristics of pluripotent stem cells continue to be identified. Pluripotent stem cell markers include, for example, the expression of one or more of the following: ABCG2, CRIPTO, FOXD3, Connexin43, Connexin45, OCT4, SOX2, Nanog, hTERT, UTF1, ZFP42, SSEA-3, SSEA-4, Tra 1-60, Tra 1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Formation of Cells Expressing Markers Characteristic of the Pancreatic Endoderm Lineage from Cells Expressing Markers Characteristic of the Definitive Endoderm Lineage Cells expressing markers characteristic of the definitive endoderm lineage may be differentiated into cells expressing markers characteristic of the pancreatic endoderm lineage by any method in the art or by any method proposed in this invention.

For example, cells expressing markers characteristic of the definitive endoderm lineage may be differentiated into cells expressing markers characteristic of the pancreatic endoderm lineage according to the methods disclosed in D'Amour et al., Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/736,908, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage with retinoic acid and at least one fibroblast growth factor for a period of time, according to the methods disclosed in U.S. patent application Ser. No. 11/779,311, assigned to LifeScan, Inc.

In one aspect of the present invention, cells expressing markers characteristic of the definitive endoderm lineage are further differentiated into cells expressing markers characteristic of the pancreatic endoderm lineage, by treating the cells expressing markers characteristic of the definitive endoderm lineage according to the methods disclosed in U.S. patent application Ser. No. 60/990,529.

Characterization of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, HLXB9, PTF1 alpha, PDX1, HNF6, HNF-1 beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Formation of Pancreatic Endocrine Precursor Cells from Cells Expressing Markers Characteristic of the Pancreatic Endoderm Lineage In one aspect of the present invention, cells expressing markers characteristic of the pancreatic endoderm lineage are differentiated into pancreatic endocrine precursor cells, by culturing the cells expressing markers characteristic of the pancreatic endoderm lineage in medium supplemented with a factor capable of inhibiting BMP and a TGF-β receptor I kinase inhibitor.

In one embodiment, the factor capable of inhibiting BMP is noggin. Noggin may be used at a concentration from about 100 pg/ml to about 500 µg/ml. In one embodiment, noggin is used at a concentration of 100 ng/ml.

In one embodiment, the TGF-β receptor I kinase inhibitor is ALK5 inhibitor II (Calbiochem, Ca). ALK5 inhibitor II may be used at a concentration from about 0.1 µM to about 10 µM. In one embodiment, ALK5 inhibitor II is used at a concentration of 1 µM.

In one embodiment, the medium is DMEM containing 4500 mg/l glucose and 1% B27.

In one embodiment, the cells are cultured in the culture medium for about four days.

The efficiency of differentiation may be determined by exposing a treated cell population to an agent (such as an antibody) that specifically recognizes a protein marker expressed by pancreatic endocrine precursor cells.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Characteristics of pluripotent stem cells are well known to those skilled in the art, and additional characteristics of pluripotent stem cells continue to be identified. Pluripotent stem cell markers include, for example, the expression of one or more of the following: ABCG2, CRIPTO, FOXD3, Connexin43, Connexin45, OCT4, SOX2, Nanog, hTERT, UTF1, ZFP42, SSEA-3, SSEA-4, Tra 1-60, Tra 1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the pancreatic endoderm lineage.

Markers characteristic of the pancreatic endoderm lineage are selected from the group consisting of PDX1, HNF-1 beta, PTF1 alpha, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of pancreatic endocrine precursor cells are selected from the group consisting of NGN3, NKX6.1, NEUROD, ISL1, PDX1, PAX4, NKX2.2, PAX6 or ARX.

Formation of Cells Expressing Markers Characteristic of the Pancreatic Endocrine Lineage from Pancreatic Endocrine Precursor Cells In one embodiment, pancreatic endocrine precursor cells, produced by the methods of the present invention may be further differentiated into cells expressing markers characteristic of the pancreatic endocrine lineage.

Pancreatic endocrine precursor cells may be differentiated into cells expressing markers characteristic of the pancreatic endocrine lineage by any method in the art or by any method proposed in this invention.

For example, pancreatic endocrine precursor cells obtained according to the methods of the present invention are further differentiated into cells expressing markers characteristic of the pancreatic endocrine lineage, by culturing the pancreatic endocrine precursor cells in medium containing exendin 4, then removing the medium containing exendin 4 and subsequently culturing the cells in medium containing exendin 1, IGF1 and HGF. An example of this method is disclosed in D' Amour et al., Nature Biotechnology, 2006.

For example, pancreatic endocrine precursor cells obtained according to the methods of the present invention are further differentiated into cells expressing markers characteristic of the pancreatic endocrine lineage, by culturing the pancreatic endocrine precursor cells in medium containing DAPT (Sigma-Aldrich, MO) and exendin 4. An example of this method is disclosed in D' Amour et al., Nature Biotechnology, 2006.

For example, pancreatic endocrine precursor cells obtained according to the methods of the present invention are further differentiated into cells expressing markers characteristic of the pancreatic endocrine lineage, by culturing the pancreatic endocrine precursor cells in medium containing exendin 4. An example of this method is disclosed in D' Amour et al., Nature Biotechnology, 2006.

For example, cells pancreatic endocrine precursor cells obtained according to the methods of the present invention are further differentiated into cells expressing markers characteristic of the pancreatic endocrine lineage, by treating the pancreatic endocrine precursor cells with a factor that inhibits the Notch signaling pathway, according to the methods disclosed in U.S. patent application Ser. No. 11/736,908, assigned to LifeScan, Inc.

For example, pancreatic endocrine precursor cells obtained according to the methods of the present invention are further differentiated into cells expressing markers characteristic of the pancreatic endocrine lineage, by treating the pancreatic endocrine precursor cells with a factor that inhibits the Notch signaling pathway, according to the methods disclosed in U.S. patent application Ser. No. 11/779,311, assigned to LifeScan, Inc.

For example, pancreatic endocrine precursor cells obtained according to the methods of the present invention are further differentiated into cells expressing markers characteristic of the pancreatic endocrine lineage, by treating the pancreatic endocrine precursor cells with a factor that inhibits the Notch signaling pathway, according to the methods disclosed in U.S. patent application Ser. No. 60/953,178, assigned to LifeScan, Inc.

For example, pancreatic endocrine precursor cells obtained according to the methods of the present invention are further differentiated into cells expressing markers characteristic of the pancreatic endocrine lineage, by treating the pancreatic endocrine precursor cells with a factor that inhibits the Notch signaling pathway, according to the methods disclosed in U.S. patent application Ser. No. 60/990,529, assigned to LifeScan, Inc.

Markers characteristic of the pancreatic endocrine lineage are selected from the group consisting of NEUROD, ISL1, PDX1, NKX6.1, PAX4, PAX6, NGN3, and NKX2.2. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NGN-3, NKX2.2, NKX6.1, NEUROD, ISL1, HNF3 beta, MAFA, PAX4, and PAX6. In one aspect of the present invention, a cell expressing markers characteristic of the β cell lineage is a β cell.

Therapies

In one aspect, the present invention provides a method for treating a patient suffering from, or at risk of developing, Type1 diabetes. In one embodiment, the method involves culturing pluripotent stem cells, differentiating the pluripotent stem cells in vitro into a β-cell lineage, and implanting the cells of a β-cell lineage into a patient. In an alternate embodiment, the method involves culturing pluripotent stem cells, differentiating the pluripotent stem cells in vitro into pancreatic endocrine precursor cells, and implanting the pancreatic endocrine precursor cells into a patient.

In yet another aspect, this invention provides a method for treating a patient suffering from, or at risk of developing, Type 2 diabetes. In one embodiment, the method involves culturing pluripotent stem cells, differentiating the pluripotent stem cells in vitro into a β-cell lineage, and implanting the cells of a β-cell lineage into a patient. In an alternate embodiment, the method involves culturing pluripotent stem cells, differentiating the pluripotent stem cells in vitro into pancreatic endocrine precursor cells, and implanting the pancreatic endocrine precursor cells into a patient.

If appropriate, the patient can be further treated with pharmaceutical agents or bioactives that facilitate the survival and function of the transplanted cells. These agents may include, for example, insulin, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -7, -8, -10, -15), vascular endothelial cell-derived growth factor (VEGF), pleiotrophin, endothelin, among others.

Other pharmaceutical compounds can include, for example, nicotinamide, glucagon like peptide-I (GLP-1) and II, GLP-1 and 2 mimetibody, Exendin-4, retinoic acid, parathyroid hormone, MAPK inhibitors, such as, for example, compounds disclosed in U.S. Published Application 2004/0209901 and U.S. Published Application 2004/0132729.

The pluripotent stem cells may be differentiated into an insulin-producing cell prior to transplantation into a recipient. In a specific embodiment, the pluripotent stem cells are fully differentiated into β-cells, prior to transplantation into a recipient. Alternatively, the pluripotent stem cells may be transplanted into a recipient in an undifferentiated or partially differentiated state. Further differentiation may take place in the recipient.

Definitive endoderm cells or, alternatively, pancreatic endoderm cells, or, alternatively, β cells, may be implanted as dispersed cells or formed into clusters that may be infused into the hepatic portal vein. Alternatively, cells may be provided in biocompatible degradable polymeric supports, porous non-degradable devices or encapsulated to protect from host immune response. Cells may be implanted into an appropriate site in a recipient. The implantation sites include, for example, the liver, natural pancreas, renal subcapsular space, omentum, peritoneum, subserosal space, intestine, stomach, or a subcutaneous pocket.

To enhance further differentiation, survival or activity of the implanted cells, additional factors, such as growth factors, antioxidants or anti-inflammatory agents, can be administered before, simultaneously with, or after the administration of the cells. In certain embodiments, growth factors are utilized to differentiate the administered cells in vivo. These factors can be secreted by endogenous cells and exposed to the administered cells in situ. Implanted cells can be induced to differentiate by any combination of endogenous and exogenously administered growth factors known in the art.

The amount of cells used in implantation depends on a number of various factors including the patient's condition and response to the therapy, and can be determined by one skilled in the art.

In one aspect, this invention provides a method for treating a patient suffering from, or at risk of developing diabetes. This method involves culturing pluripotent stem cells, differentiating the cultured cells in vitro into a β-cell lineage, and incorporating the cells into a three-dimensional support. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells.

Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, for example, the materials disclosed in U.S. Pat. Nos. 5,770,417, 6,022,743, 5,567,612, 5,759,830, 6,626,950, 6,534,084, 6,306,424, 6,365,149, 6,599,323, 6,656,488, U.S. Published Application 2004/0062753 A1, U.S. Pat. Nos. 4,557,264 and 6,333,029.

To form a support incorporated with a pharmaceutical agent, the pharmaceutical agent can be mixed with the polymer solution prior to forming the support. Alternatively, a pharmaceutical agent could be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

The support may be incorporated with at least one pharmaceutical compound that is an anti-apoptotic compound, such as, for example, compounds disclosed in U.S. Pat. No. 6,793,945.

The support may also be incorporated with at least one pharmaceutical compound that is an inhibitor of fibrosis, such as, for example, compounds disclosed in U.S. Pat. No. 6,331,298.

The support may also be incorporated with at least one pharmaceutical compound that is capable of enhancing angiogenesis, such as, for example, compounds disclosed in U.S. Published Application 2004/0220393 and U.S. Published Application 2004/0209901.

The support may also be incorporated with at least one pharmaceutical compound that is an immunosuppressive compound, such as, for example, compounds disclosed in U.S. Published Application 2004/0171623.

The support may also be incorporated with at least one pharmaceutical compound that is a growth factor, such as, for example, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, nodal, noggin, NGF, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a scaffold can be achieved by the simple depositing of cells onto the scaffold. Cells can enter into the scaffold by simple diffusion (J. Pediatr. Surg. 23 (1 Pt 2): 3-9 (1988)). Several other approaches have been developed to enhance the efficiency of cell seeding. For example, spinner flasks have been used in seeding of chondrocytes onto polyglycolic acid scaffolds (Biotechnol. Prog. 14(2): 193-202 (1998)). Another approach for seeding cells is the use of centrifugation, which yields minimum stress to the seeded cells and enhances seeding efficiency. For example, Yang et al. developed a cell seeding method (J. Biomed. Mater. Res. 55(3): 379-86 (2001)), referred to as Centrifugational Cell Immobilization (CCI).

The present invention is further illustrated, but not limited by, the following examples.

EXAMPLES

Example 1

Formation of a Population of Pancreatic Endocrine Precursor Cells

Cells of the human embryonic stem cell line H1 were cultured on MATRIGEL-coated plates (1:30 dilution), and differentiated into pancreatic endocrine precursor cells using the following protocol:

a. RPMI medium (Catalogue #22400, Invitrogen, Ca) supplemented with 2% BSA (Catalog #152401, MP Biomedical, Ohio), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day followed by treatment with RPMI media supplemented with 2% BSA and 100 ng/ml activin A plus 8 ng/ml of bFGF for an additional two days (Stage 1), then b. DMEM/F12 (Catalogue #11330, Invitrogen, Ca)+2% BSA+50 ng/ml FGF7 for three days (Stage 2), then c. Different basal media indicated in Table 1 were used, supplemented with 1% B27 (#17504-044, Invitrogen, CA)+50 ng/ml FGF7+0.25 µM Cyclopamine-KAAD (#239804, Calbiochem, CA)+2 µM Retinoic acid (RA) (Sigma, MO)+100 ng/ml of Noggin (R & D Systems, MN) for four days (Stage 3), then d. Different basal media indicated in Table 1 were used, supplemented with 1% B27 (Invitrogen, CA)+100 ng/ml Noggin+1 µM ALK5 inhibitor II (Catalog #616452, Calbiochem, Ca) for three days (Stage 4).

TABLE 1

|  | Basal Media (Stage 3) | Basal Media (Stage 4) | Catalogue# (Invitrogen, CA) |
|---|---|---|---|
| Treatment 1 | DMEM (High Glucose) | DMEM (High Glucose) | 11995-040 |
| Treatment 2 | DMEM (Low Glucose) | DMEM (Low Glucose) | 10567-014 |
| Treatment 3 | CMRL | CMRL | 11530-037 |
| Treatment 4 | DMEM/F12 | DMEM/F12 | 11039-021 |

Cultures were sampled in duplicate at stage four day three of differentiation and analyzed for expression of pancreatic markers using real-time PCR. In parallel, stage four, day three cultures were fixed and stained for the following proteins: NKX6.1 (Catalogue #F64A6B4, Developmental Studies Hybridoma Bank, University of Iowa), PDX1, NGN3, and CDX2.

Figure 2A:
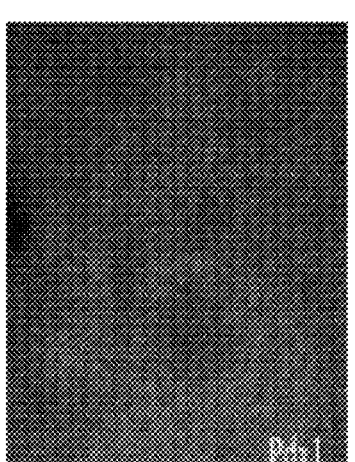
FIGS. 2A-2H show immunofluorescence images of the pancreatic marker PDX1 (FIGS. 2A-2B), NKX6.1 (FIGS. 2C-2D), CDX2 (FIGS. 2E-2F) and NGN3 (FIGS. 2G-2H) for cells treated with DMEM/F12 (FIGS. 2A, 2C, 2E, 2G) and cells treated with DMEM-high glucose (FIGS. 2B, 2D, 2F, 2H) at stage 4 day 3, treated as described in Example 1.
Figure 2B:
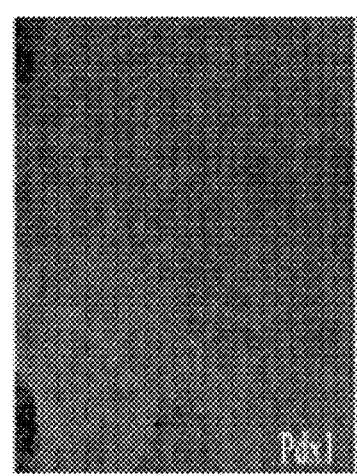
Figure 2C:
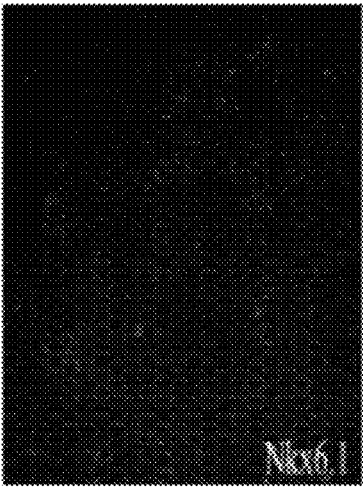
Figure 2D:
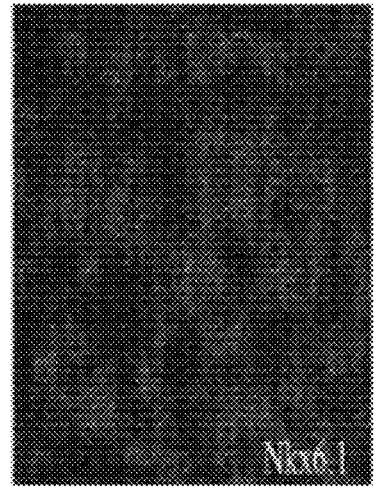
Figure 2E:
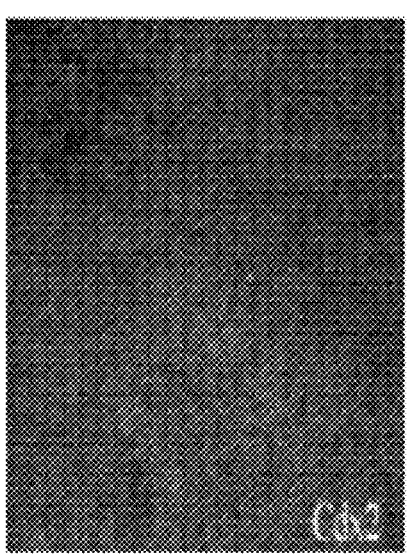
Figure 2F:
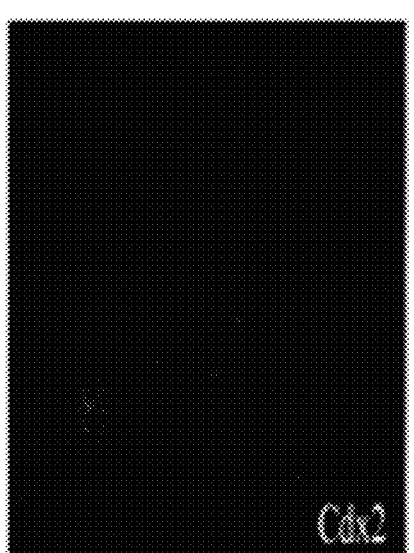
Figure 2G:
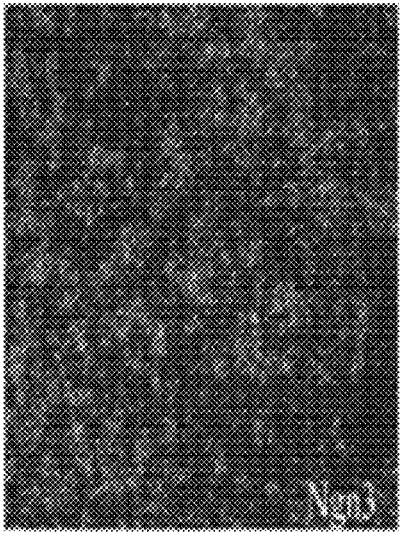

Stage four, day three samples, cultured in DMEM medium (treatment 1 and treatment 2, Table 1), showed significant increases in the level of NKX6.1, NGN3 and PTF1 alpha expression by PCR (FIG. 1) compared to cells cultured in DMEM/F12 (treatment 4, table 1) or CMRL (treatment 3, Table 1). No differences in the level of PDX1 expression was observed in the cultures tested. However, immunocytochemistry revealed that cells cultured in DMEM/F12 medium, a large proportion of PDX1 expressing cells also expressed CDX2, a marker for gut endoderm (FIGS. 2A, 2E). In contrast, the cells treated in DMEM medium provided a separation of PDX1 positive cells and CDX2 positive cells (FIGS. 2B, 2F), wherein a large proportion of PDX1 expressing cells did not express CDX2.

Figure 2H:
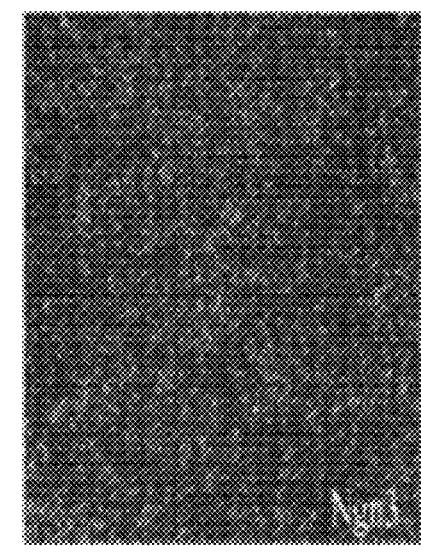

In addition, cells expressing PDX1 that were obtained from cells treated in DMEM also expressed NKX6.1. As seen in FIG. 2, 50 to 60% of the PDX1 positive cells also expressed NKX6.1 by the end of stage 4 (FIG. 2D) and 20 to 30% of the PDX1 positive cells expressed NGN3 (FIG. 2H). However, co-expression of NKX6.1 and NGN3 was not observed in cells cultured in DMEM. The co-expression of PDX1 and NGN3 was also observed in cells cultured in DMEM/F12 or CMRL medium (FIG. 2G), however, the expression of NKX6.1 was not observed in cells treated in either DMEM/F12 or CMRL medium (FIG. 2C).

These data suggest that different basal medium facilitate the generation of different pancreatic endoderm cell populations: By using DMEM/F12, a population that co-expresses PDX1 and CDX2 was generated, while the use of DMEM resulted in a population that expressed PDX1 and NKX6.1, but did not express CDX2. Further, the data suggests that the expression of pancreatic gene expression was increased by increasing the glucose concentration of the culture medium. See FIG. 1 and FIG. 2

Example 2

Direct Differentiation of Human Embryonic Stem Cells to Pancreatic Endocrine Precursor Cells Cells of the human embryonic stem cell line H1 were cultured on MATRIGEL-coated plates (1:30 dilution), and differentiated into pancreatic endocrine precursor cells using the following protocol:

a. RPMI medium (Catalogue #22400, Invitrogen, Ca) supplemented with 2% BSA (Catalog #152401, MP Biomedical, Ohio), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day followed by treatment with RPMI media supplemented with 2% BSA and 100 ng/ml activin A plus 8 ng/ml of bFGF for an additional two days (Stage 1), then b. DMEM/F12 (Catalogue #11330, Invitrogen, Ca)+2% BSA+50 ng/ml FGF7 for three days (Stage 2), then c. DMEM (high glucose)+1% B27 (Invitrogen, CA)+50 ng/ml FGF7+0.25 µM Cyclopamine-KAAD+2 µM Retinoic acid (RA) (Sigma, MO)+100 ng/ml of Noggin (R & D Systems, MN) for four days (Stage 3), then d. DMEM (high glucose)+1% B27 (Invitrogen, CA)+100 ng/ml Noggin+1 µM ALK5 inhibitor II (Catalog #616452, Calbiochem, Ca) for three days (Stage 4), then e. DMEM (high glucose)+0.5% ITS (Invitrogen, CA)+0.1% BSA+1 µM Alk5 inhibitor II+100 ng/ml Noggin+20 ng/ml Betacellulin (R&D Systems, MN) for five days (Stage 5).

Figure 3A:
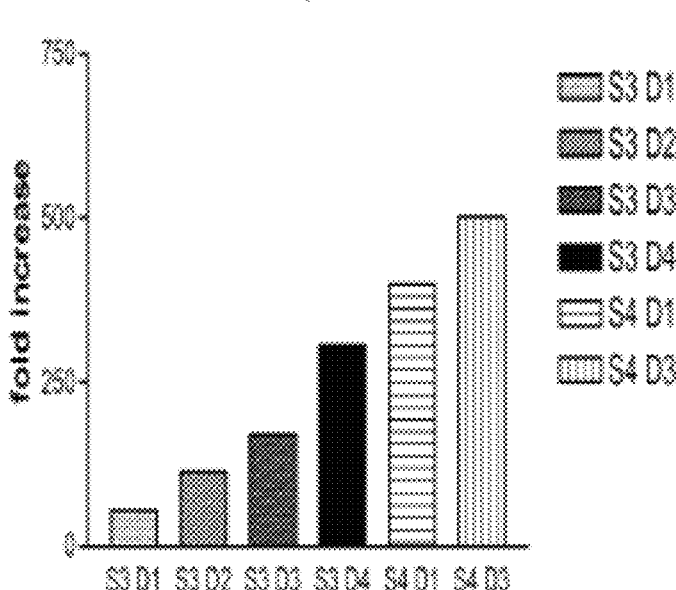
FIGS. 3A-3F show the expression of PDX1 (FIG. 3A), NKX6.1 (FIG. 3B), PTF1 alpha (FIG. 3C), NGN3 (FIG. 3D), PAX4 (FIG. 3E) and NKX2.2 (FIG. 3F) from samples of cells treated according to the methods described in Example 2. Duplicate samples were collected for real-time PCR analysis at the indicated times. The plots represent fold induction for each gene relative to the expression of genes at stage 3 day 1.
Figure 3B:
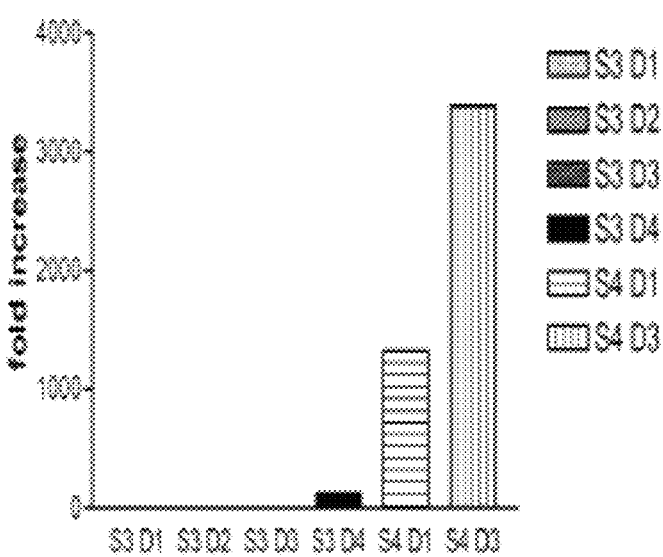
Figure 3C:
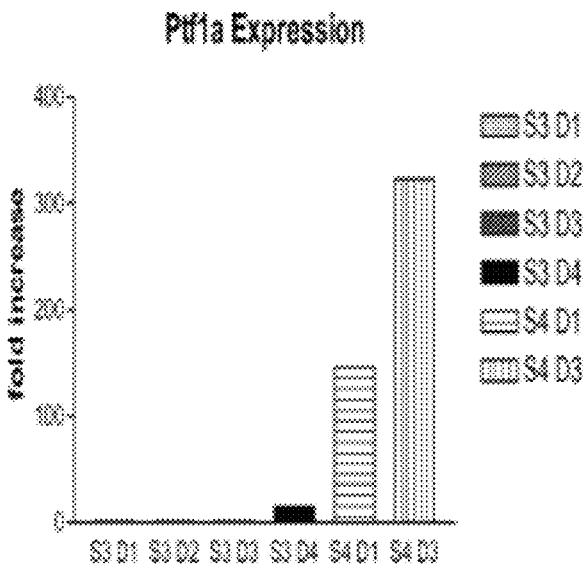
Figure 3D:
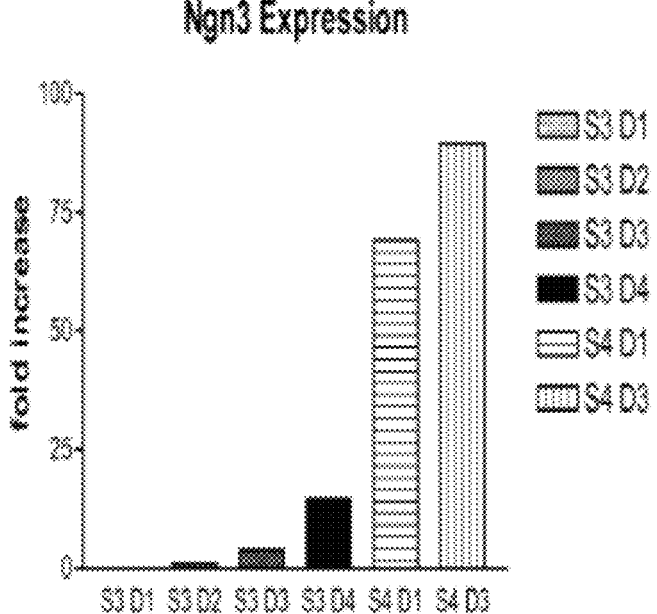
Figure 3E:
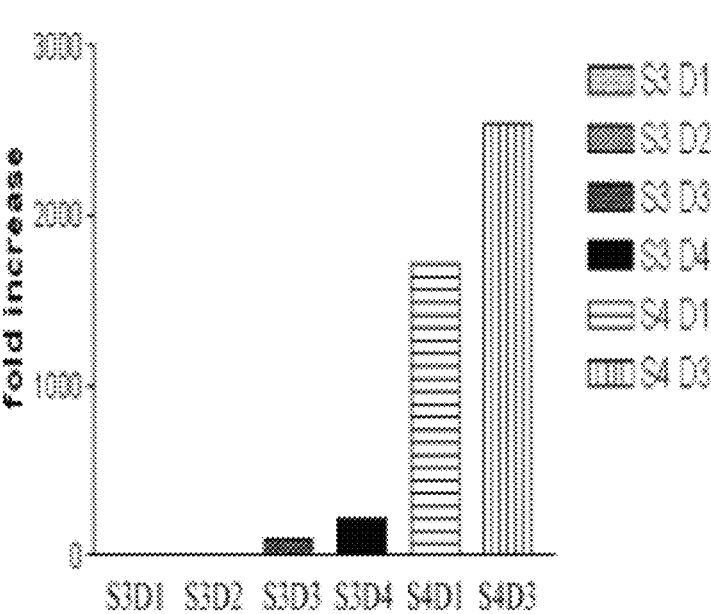
Figure 3F:
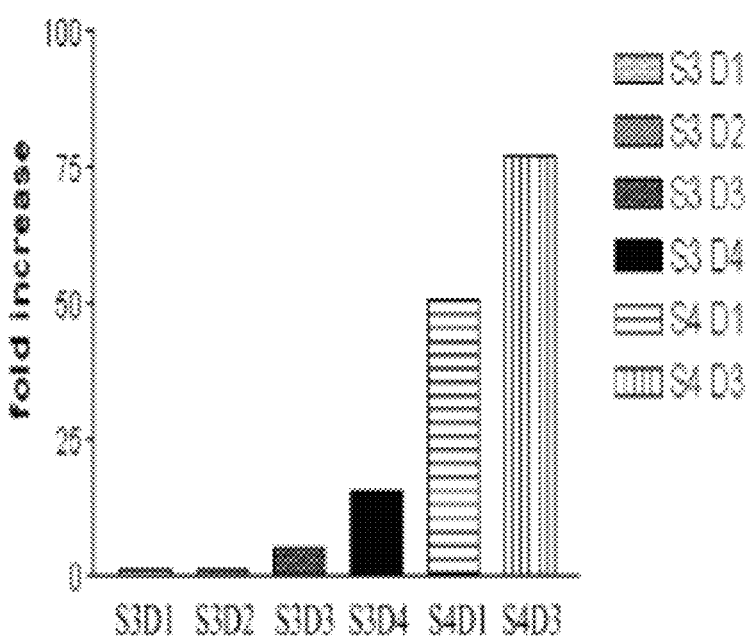

Cultures were sampled in duplicate each day from stage 2 day 3 to stage four day 3 of differentiation and analyzed for expression of pancreatic markers using real-time PCR. After the cells entered stage 4, a dramatic increase of PDX1, NKX6.1 and PTF1 alpha was observed (FIGS. 3A-3C). In addition, a significant up-regulation of NGN3, PAX4, NKX2.2 and NEUROD was also observed (FIGS. 3D-3F). PAX4, NKX2.2 and NEUROD, are directly regulated by NGN3, which suggests that the pancreatic endoderm initiated the commitment to the pancreatic endocrine lineage.

Figure 4:
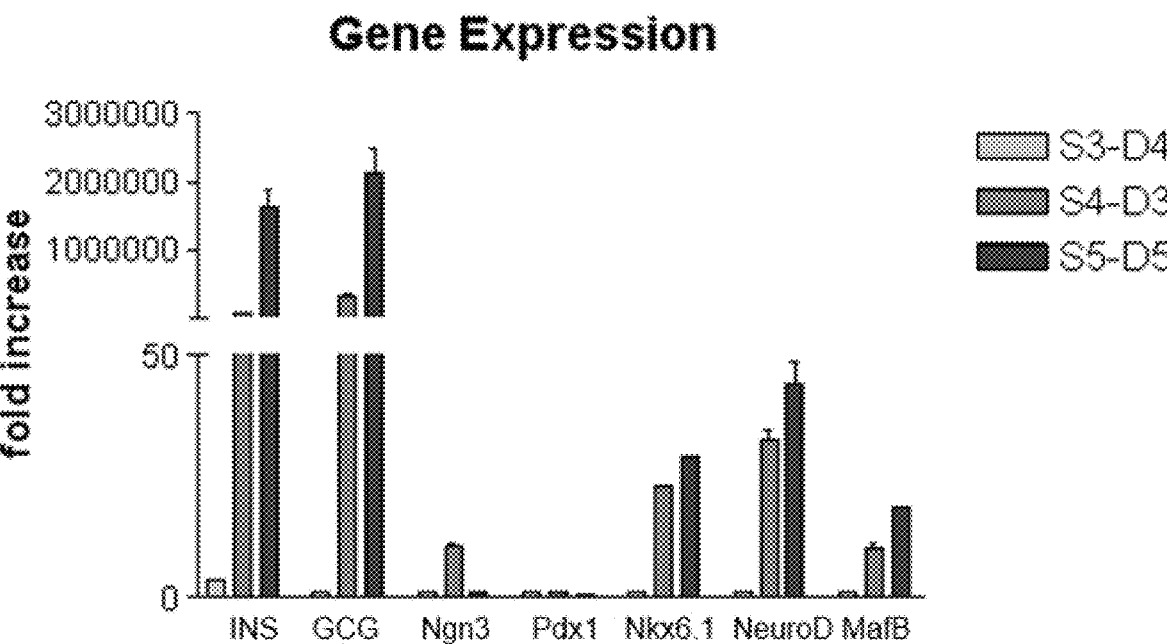
FIG. 4 shows the expression of insulin (INS), glucagon (GCG), PDX1, NKX6.1, NGN3, MAFB and NEUROD in cells treated according to the methods described in Example 2. Duplicate samples were collected for real-time PCR analysis. The plots represent fold induction for each gene relative to the expression of genes at stage 3 day 4. The light gray bars represent data from samples taken from cells harvested at stage 3 day 4. The dark gray bars represent data from samples taken from cells harvested at stage 4 day 3. The black bars represent data from samples taken from cells harvested at stage 5 day 5.

Further differentiation of the pancreatic endocrine precursor cells in vitro into insulin expressing cells was achieved by the addition of a TGF-β receptor I kinase inhibitor, Noggin and Betacellulin. As shown in FIG. 4, a significant increase in insulin expression was observed following the addition of Alk5 inhibitor II (a TGF-β receptor I kinase inhibitor), Noggin and Betacellulin for five days. NGN3 and PAX4 expression levels declined, while the level of expression of PDX1, NKX6.1 MAFB and NEUROD remained constant.

Example 3

An Alternate Method for the Direct Differentiation of Human Embryonic Stem Cells to Pancreatic Endocrine Precursor Cells This example demonstrates an alternative method for differentiating human embryonic stem cells to pancreatic endocrine precursors using Alk5 inhibitor II (an inhibitor of TGF-beta receptor family), together with a low dose of exogenous retinoid, for example retinol (vitamin A), which may be present in media supplements such as B27.

Cells of the human embryonic stem cell line H1 at passages 45 were cultured on MATRIGEL-coated plates (1:30 dilution), and differentiated into pancreatic endocrine precursor cells using the following protocol:

a. RPMI medium supplemented with 2% BSA, and 100 ng/ml activin A plus 20 ng/ml WNT-3a plus 8 ng/ml of bFGF, for one day followed by treatment with RPMI media supplemented with 2% BSA and 100 ng/ml activin A plus 8 ng/ml of bFGF for an additional two days (Stage 1), then b. DMEM/F12+2% BSA+50 ng/ml FGF7 for three days (Stage 2), then c. DMEM (high glucose)+1% B27 (Invitrogen, CA)+50 ng/ml FGF7+0.25 μM Cyclopamine-KAAD+0.1 μM Retinoic acid (RA)+100 ng/ml Noggin for four days (Treatment 1, Stage 3), or d. DMEM (high glucose)+1% B27 (Invitrogen, CA)+50 ng/ml FGF7+0.25 μM Cyclopamine-KAAD+0.1 μM Retinoic acid (RA)+1 μM Alk5 inhibitor+Noggin 100 ng/ml for four days (Treatment 2, Stage 3), or e. DMEM (high glucose)+1% B27 (Invitrogen, CA)+50 ng/ml FGF7+0.25 μM Cyclopamine-KAAD+1 μM Alk5 inhibitor+100 ng/ml Noggin for four days (Treatment 3, Stage 3), or f. DMEM (high glucose)+1% B27 (Invitrogen, CA)+50 ng/ml FGF7+0.25 μM Cyclopamine-KAAD+2 μM Retinoic acid (RA)+100 ng/ml Noggin for four days (Treatment 4, Stage 3), then g. DMEM (high glucose)+1% B27 (Invitrogen, CA)+100 ng/ml Noggin+1 μM ALK5 inhibitor II for eight days (Stage 4).

Cultures were sampled in duplicate on day 3 and day 8 of stage 4 of differentiation, and analyzed for expression of pancreatic markers using real-time PCR.

Figure 5A:
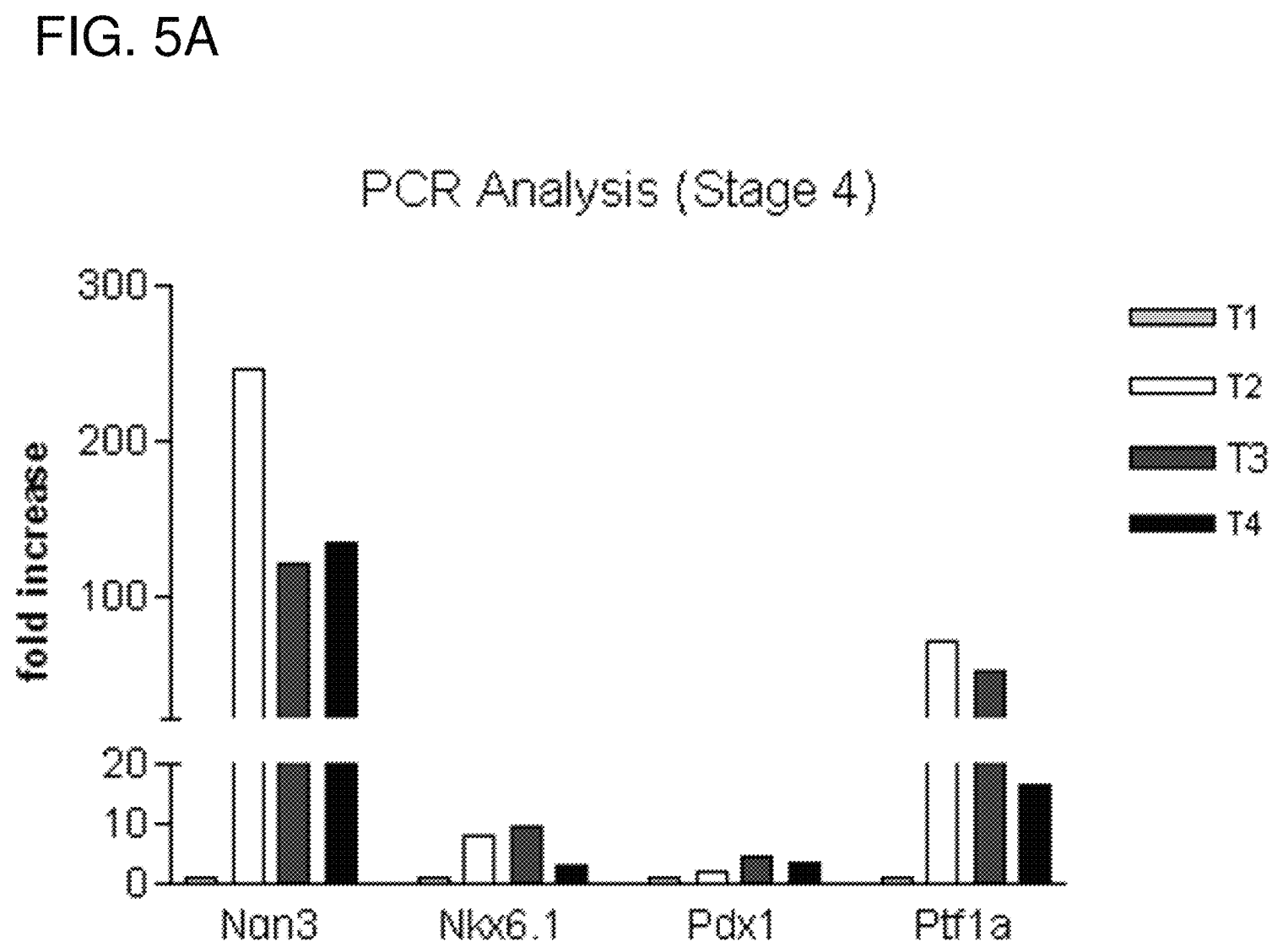
Figure 5B:
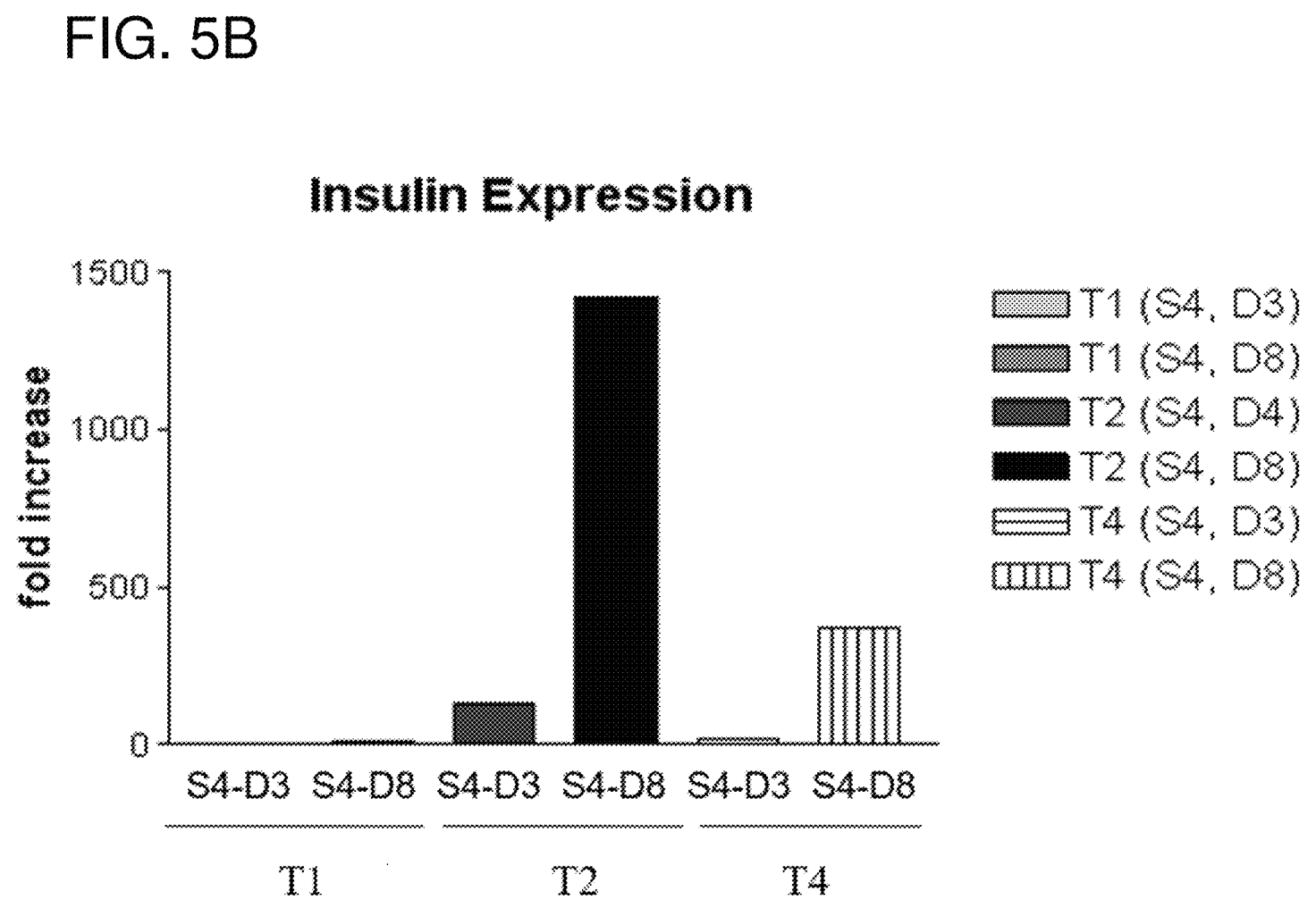

Treatment of cells expressing markers characteristic of the pancreatic endoderm lineage in medium supplemented with FGF7, Noggin and Cyclopamine-KAAD, ALK5 inhibitor II and with either low dose retinoic acid (0.1 μM) or no exogenous retinoic acid, induced the expression of NGN3 and continued up regulation of PDX1 and NKX6.1 (FIG. 5A, Treatment 3 and 4). The level of expression of NGN3 was similar in cells treated with a high dose (2 μM) of retinoic acid (FIG. 5A, Treatment 4 respectively). These data suggest that the addition of Alk5 inhibitor II is sufficient to induce the formation of pancreatic endocrine progenitor cells, when cells expressing markers characteristic of the pancreatic endoderm lineage are treated with FGF7, Noggin and Cyclopamine-KAAD. See FIG. 5A, where no expression of NGN3 was observed in cells treated with a low dose of retinoic acid (0.1 μM) in the absence of Alk5 inhibitor II (FIG. 5A, Treatment 1). The pancreatic endocrine cells formed by the above treatment were competent to form insulin expressing cells in vitro. See FIG. 5B, wherein the NGN3 expressing cells formed expressed insulin following treatment with DMEM (high glucose)+1% B27 (Invitrogen, CA)+100 ng/ml Noggin+1 μM ALK5 inhibitor II for eight days.

Example 4

In Vivo Maturation of Pancreatic Endocrine Precursor Cells

Cells of the human embryonic stem cell line H1 at passages 45 were cultured on MATRIGEL-coated plates (1:30 dilution), and differentiated into pancreatic endocrine precursor cells using the following protocol:

a. RPMI medium+2% BSA+100 ng/ml activin A+20 ng/ml WNT-3a+8 ng/ml of bFGF for one day followed by treatment with RPMI media+2% BSA+100 ng/ml activin A+8 ng/ml of bFGF for an additional two days (Stage 1), then b. DMEM/F12+2% BSA+50 ng/ml FGF7 for three days (Stage 2), then c. DMEM-High glucose+1% B27+50 ng/ml FGF7+0.25 μM Cyclopamine-KAAD+2 M Retinoic acid (RA)+100 ng/ml of Noggin for four days (Stage 3), then d. DMEM-High glucose+1% B27+100 ng/ml Noggin+1 μM ALK5 inhibitor II for three days (Stage 4).

Figure 6:
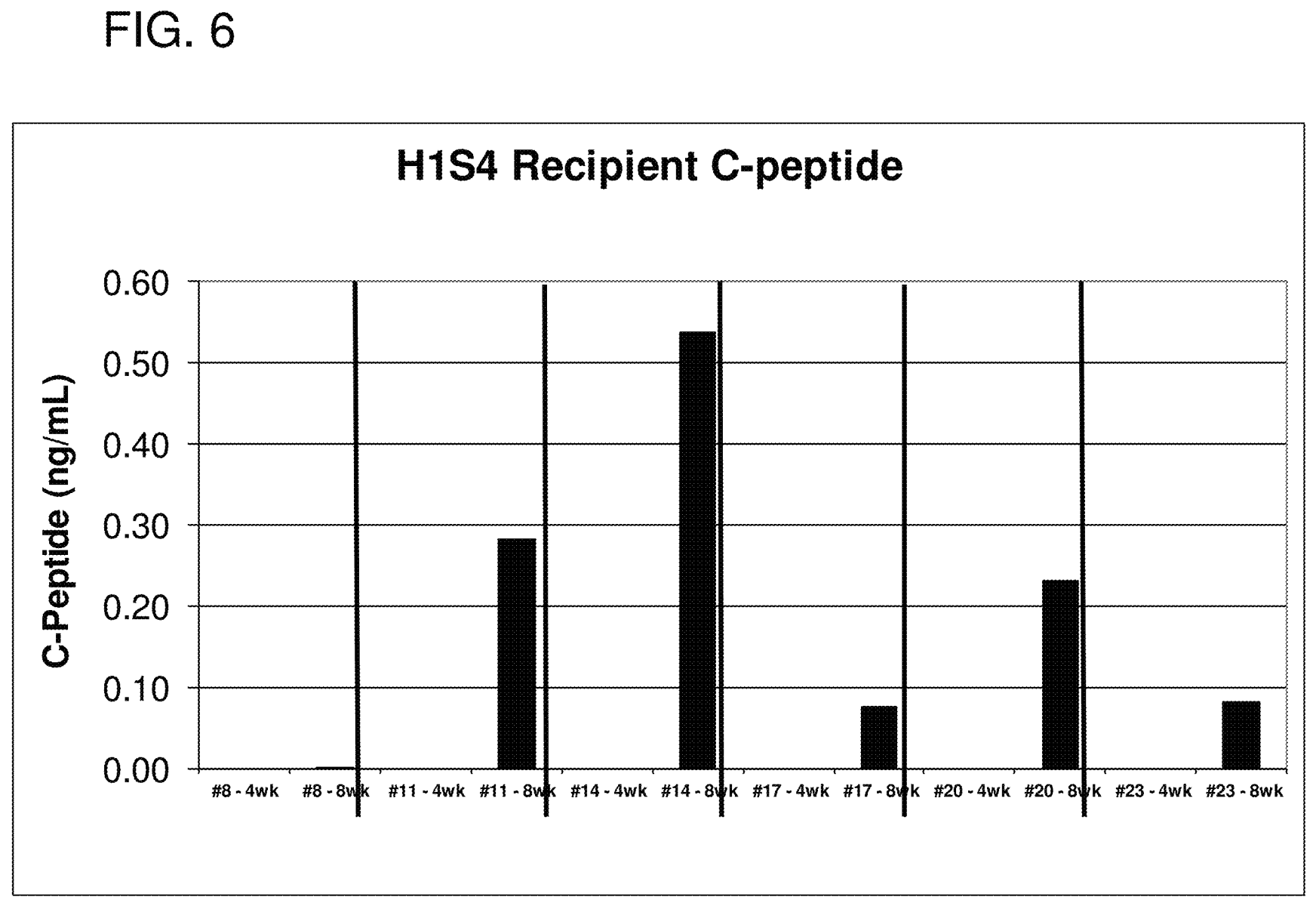

The above method (method 1) of culturing the cells in vitro was used for the transplantations in Animal Nos. 8, 11, 14, 17, 20 and 23. See FIG. 6.

An alternate differentiation protocol was also tested, wherein cells of the human embryonic stem cell line H1 at passages 45 were cultured on MATRIGEL-coated plates (1:30 dilution), and differentiated into pancreatic endocrine precursor cells using the following protocol:

a. RPMI medium+2% BSA+100 ng/ml activin A+20 ng/ml WNT-3a+8 ng/ml of bFGF for one day followed by treatment with RPMI media+2% BSA+100 ng/ml activin A+8 ng/ml of bFGF for an additional two days (Stage 1), then b. DMEM/F12+2% BSA+50 ng/ml FGF7 for three days (Stage 2), then c. DMEM (high-glucose)+1% B27+50 ng/ml FGF7+0.25 μM Cyclopamine-KAAD+2 μM Retinoic acid (RA)+100 ng/ml of Noggin+Alk5 inhibitor II 1 μM for four days (stage 3), then d. DMEM (high-glucose)+1% B27+100 ng/ml Noggin+Alk5 inhibitor II 1 μM for three days (stage 4).

Figure 7A:
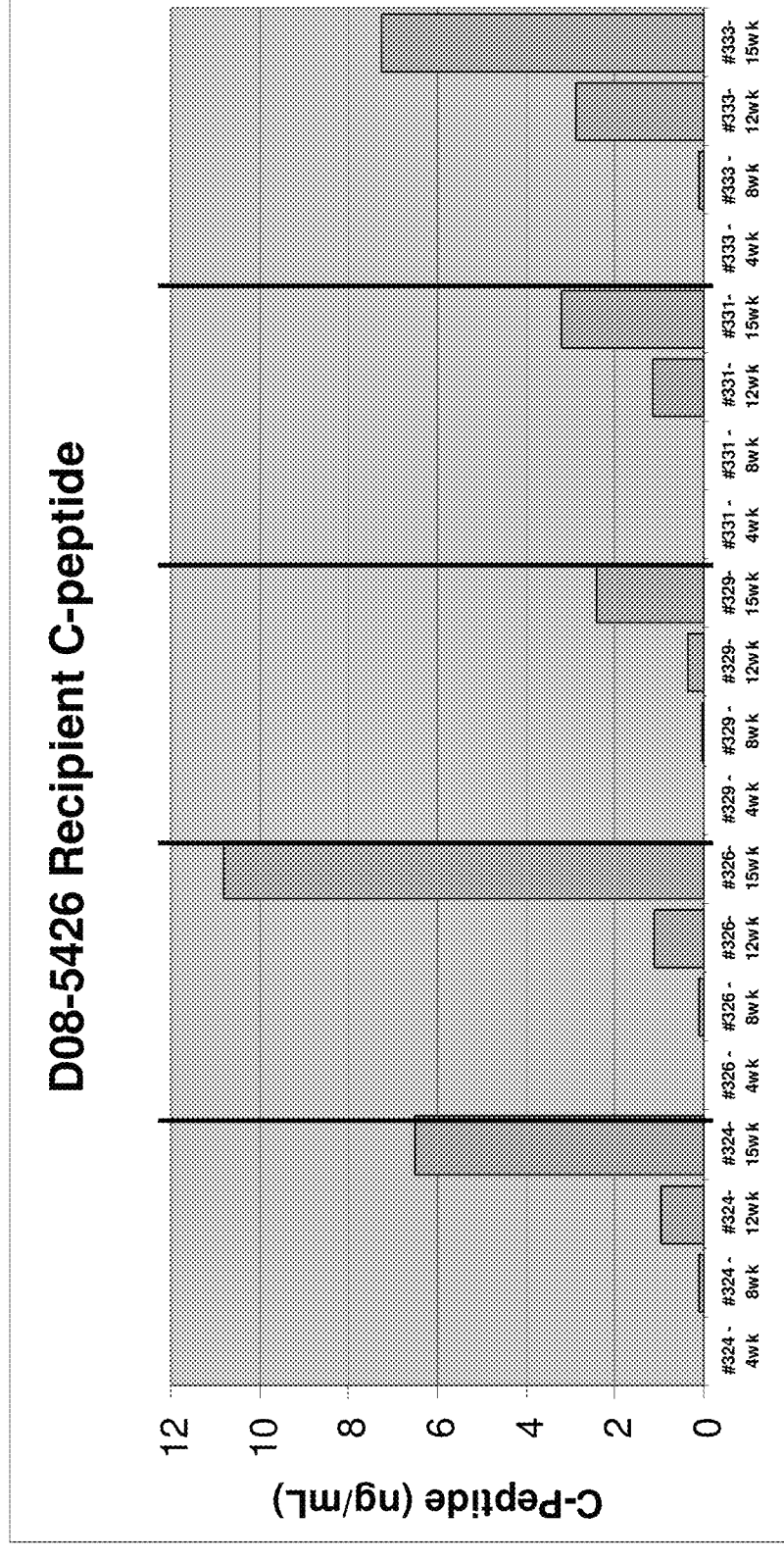
FIGS. 7A-7B show glucose stimulated of human C-peptide release kinetics of transplanted endocrine precursor cells. Specifically shown are the levels of human C-peptide (y-axis) 60 minutes after glucose administration (FIG. 7A), and the levels of human C-peptide before and after glucose administration (FIG. 7B). The x-axis indicates the animal number and days post-transplant.

Cells at the end of stage four were mechanically scored using a 1-ml glass pipette and subsequently transferred to non-adherent plates for culture overnight. The resultant aggregates were collected, and aggregates, containing 5 to 8 million cells were transplanted into the kidney capsule of an immuno-compromised mice (SCID/Bg) mouse. This method (method 2) of culturing the cells in vitro was used for the transplantations in Animal Nos. 324,326,329,331, 333. See FIGS. 7A-7B.

An alternate differentiation protocol was also tested, wherein cells of the human embryonic stem cell line H1 at passages 45 were cultured on MATRIGEL-coated plates (1:30 dilution), and differentiated into pancreatic endocrine precursor cells using the following protocol:

a. RPMI medium+2% BSA+100 ng/ml activin A+20 ng/ml WNT-3a+8 ng/ml of bFGF for one day followed by treatment with RPMI media+2% BSA+100 ng/ml activin A+8 ng/ml of bFGF for an additional two days (Stage 1), then b. DMEM/F12+2% BSA+50 ng/ml FGF7 for three days (Stage 2), then c. Culturing the cells for four days in DMEM (high-glucose)+1% B27+50 ng/ml FGF7+0.25 μM Cyclo-pamine-KAAD+0.1 μM Retinoic acid (RA)+100 ng/ml of Noggin+Alk5 inhibitor II 1 μM (stage 3), then d. DMEM (high-glucose)+1% B27 for three days (stage 4).

Figure 8:
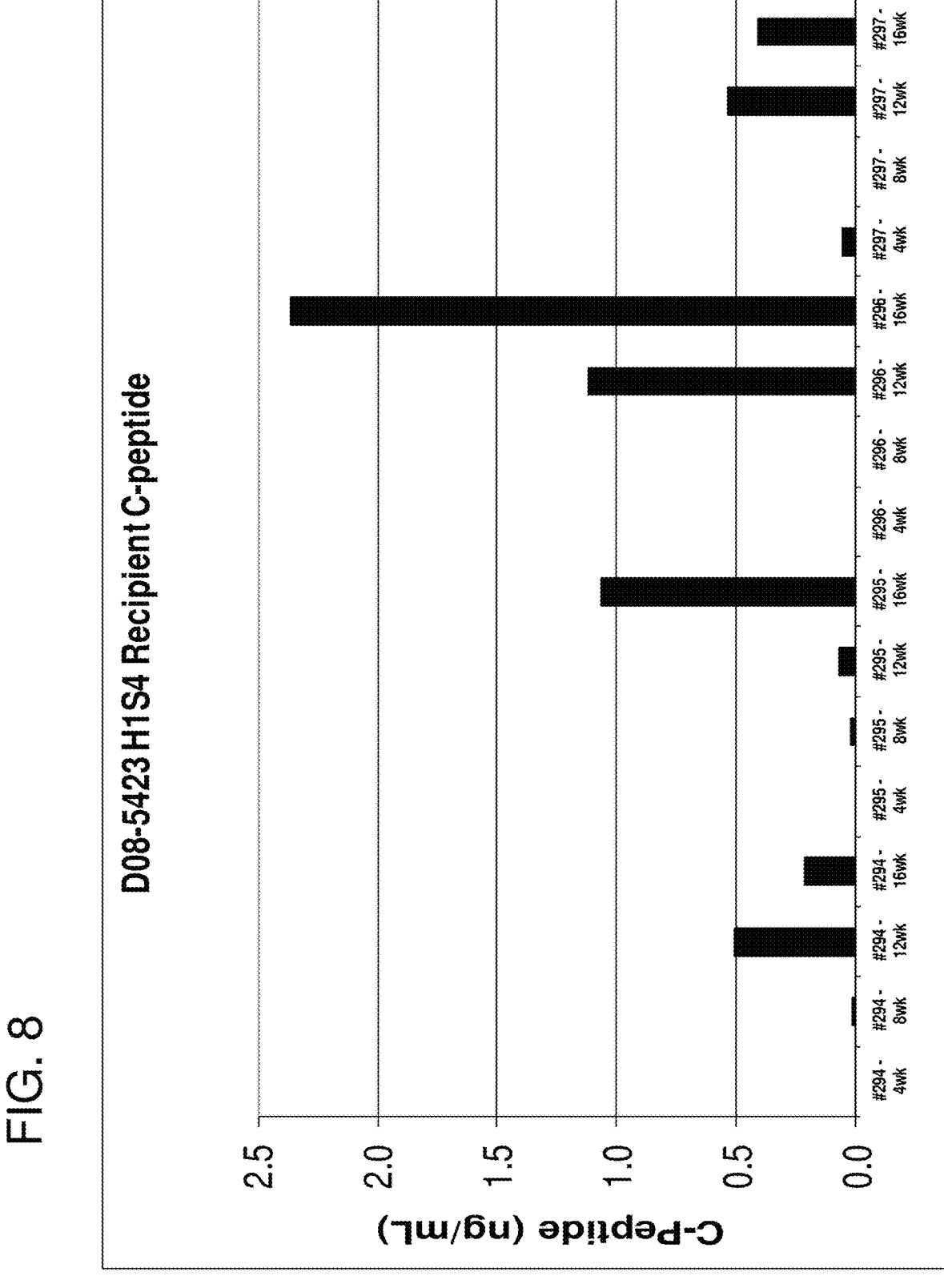
FIG. 8 shows glucose stimulated of human C-peptide release kinetics of transplanted endocrine precursor cells. Specifically shown are the levels of human C-peptide (y-axis) 60 minutes after glucose administration. The x-axis indicates the animal number and days post-transplant.

Cells at the end of stage four were mechanically scored using a 1-ml glass pipette and subsequently transferred to non-adherent plates for culture overnight. The resultant aggregates were collected, and aggregates, containing 5 to 8 million cells were transplanted into the kidney capsule of an immuno-compromised mice (SCID/Bg) mouse. This method (method 3) of culturing the cells in vitro was used for the transplantations in Animal Nos. 294, 295, 296, 297. See FIG. 8.

An alternate differentiation protocol was also tested, wherein cells of the human embryonic stem cell line H1 at passages 45 were cultured on MATRIGEL-coated plates (1:30 dilution), and differentiated into pancreatic endocrine precursor cells using the following protocol:

a. RPMI medium+2% BSA+100 ng/ml activin A+20 ng/ml WNT-3a+8 ng/ml of bFGF for one day followed by treatment with RPMI media+2% BSA+100 ng/ml activin A+8 ng/ml of bFGF for an additional two days (Stage 1), then b. DMEM/F12+2% BSA+50 ng/ml FGF7 for three days (Stage 2), then c. Culturing the cells for four days in DMEM (high-glucose)+1% B27+50 ng/ml FGF7+0.25 μM Cyclo-pamine-KAAD+0.1 μM Retinoic acid (RA)+100 ng/ml of Noggin+Alk5 inhibitor II 1 μM (stage 3), then d. DMEM (high-glucose)+1% B27+100 ng/ml of Nog-gin+Alk5 inhibitor II 1 μM for three days (stage 4).

Figure 9A:
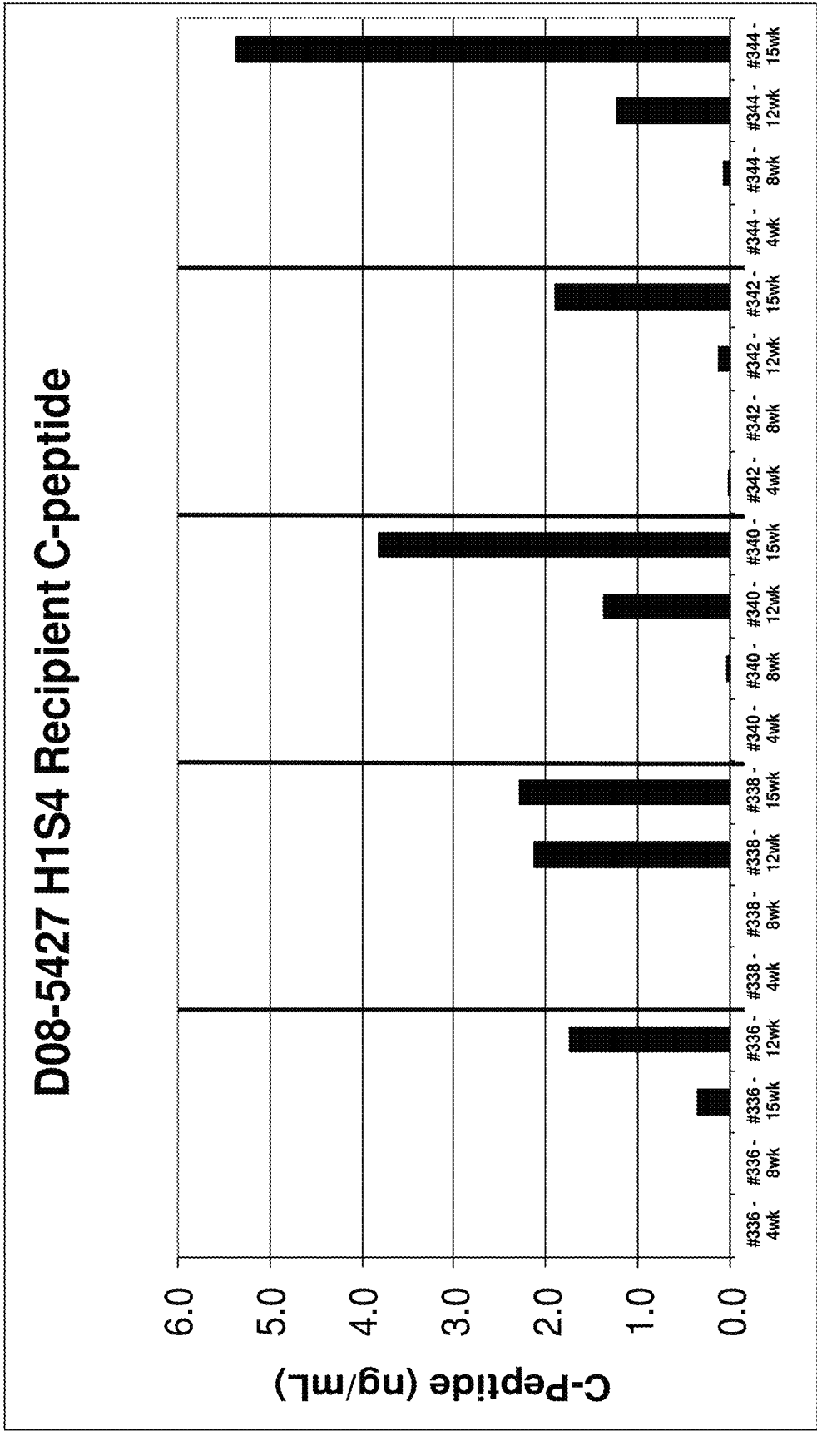
FIGS. 9A-9B show glucose stimulated of human C-peptide release kinetics of transplanted endocrine precursor cells. Specifically shown are the levels of human C-peptide (y-axis) 60 minutes after glucose administration (FIG. 9A), and the levels of human C-peptide before and after glucose administration (FIG. 9B). The x-axis indicates the animal number and days post-transplant.

Cells at the end of stage four were mechanically scored using a 1-ml glass pipette and subsequently transferred to non-adherent plates for culture overnight. The resultant aggregates were collected, and aggregates, containing 5 to 8 million cells were transplanted into the kidney capsule of an immuno-compromised mice (SCID/Bg) mouse. This method (method 4) of culturing the cells in vitro was used for the transplantations in Animal Nos. 336, 338, 340, 342, 344. See FIGS. 9A-9B.

An alternate differentiation protocol was also tested, wherein cells of the human embryonic stem cell line H1 at passages 45 were cultured on MATRIGEL-coated plates (1:30 dilution), and differentiated into pancreatic endocrine precursor cells using the following protocol:

a. RPMI medium+2% BSA+100 ng/ml activin A+20 ng/ml WNT-3a+8 ng/ml of bFGF for one day followed by treatment with RPMI media+2% BSA+100 ng/ml activin A+8 ng/ml of bFGF for an additional two days (Stage 1), then b. DMEM/F12+2% BSA+50 ng/ml FGF7 for three days (Stage 2), then c. Culturing the cells for four days in DMEM (high-glucose)+1% B27+50 ng/ml FGF7+0.25 μM Cyclo-pamine-KAAD+100 ng/ml of Noggin+Alk5 inhibitor II 1 μM (stage 3), then d. DMEM (high-glucose)+1% B27+100 ng/ml Noggin+ Alk5 inhibitor II (stage 4).

Figure 10A:
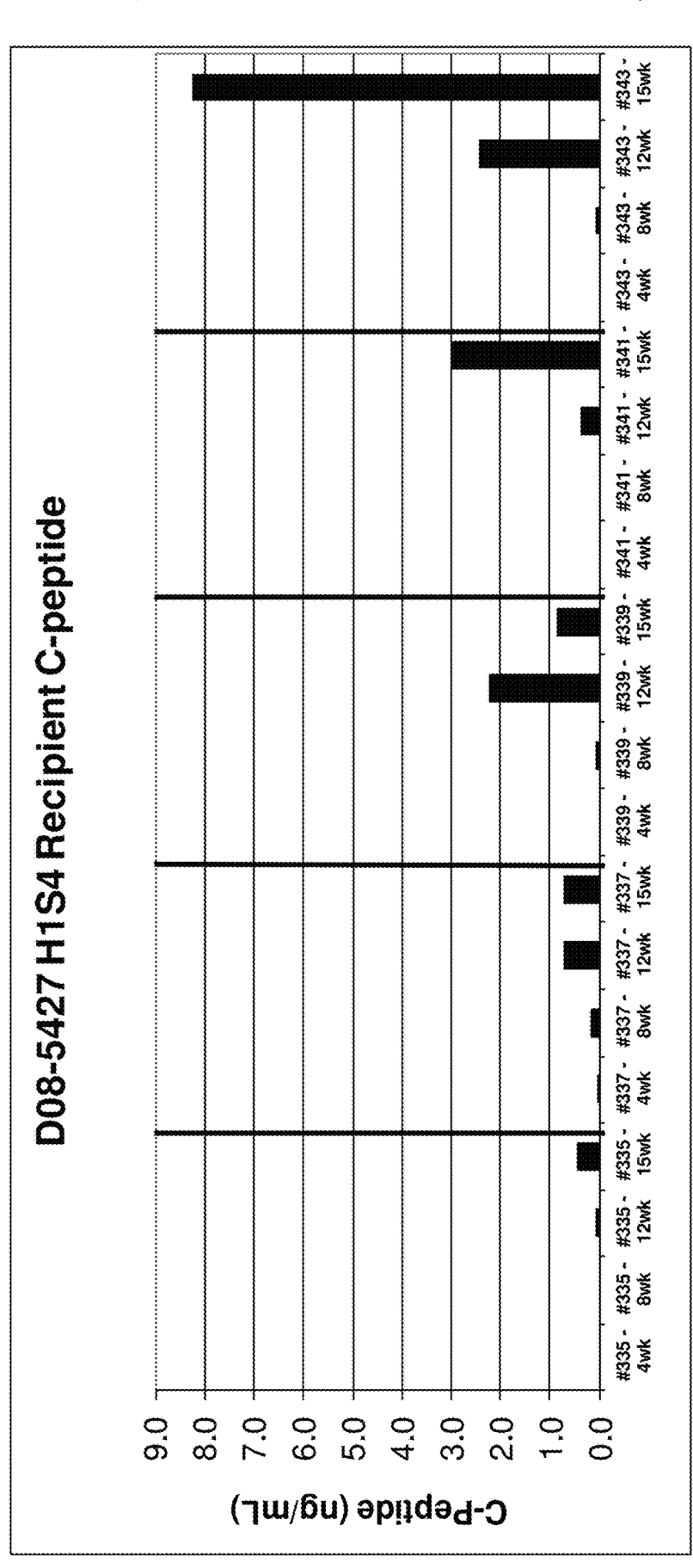
FIGS. 10A-10B shows glucose stimulated of human C-peptide release kinetics of transplanted endocrine precursor cells. Specifically shown are the levels of human C-peptide (y-axis) 60 minutes after glucose administration (FIG. 10A), and the levels of human C-peptide before and after glucose administration (FIG. 10B). The x-axis indicates the animal number and days post-transplant.

Cells at the end of stage four were mechanically scored using a 1-ml glass pipette and subsequently transferred to non-adherent plates for culture overnight. The resultant aggregates were collected, and aggregates, containing 5 to 8 million cells were transplanted into the kidney capsule of an immuno-compromised mice (SCID/Bg) mouse. This method (method 5) of culturing the cells in vitro was used for the transplantations in Animal Nos. 335,337,339,341, 343. See FIGS. 10A-10B.

Five to six-week-old male scid-beige mice (C.B-Igh-1b/GbmsTac-Prkdc$^{scid}$-Lyst$^{bg}$ N7) were purchased from Taconic Farms. Mice were housed in microisolator cages with free access to sterilized food and water. In preparation for surgery, mice were identified by ear tagging and their body weight measured and their blood glucose determine by a hand held glucometer (One Touch, LifeScan).

Mice were anesthetized with a mixture of isoflurane and oxygen and the surgical site was shaved with small animal clippers. Mice were dosed with 0.1 mg·kg Buprenex sub-cutaneously pre-operatively. The surgical site was prepared with successive washes of 70% isopropyl alcohol and 10% povidone-iodide.

Cells at the end of stage four were briefly treated with 1 mg/ml dispase for five minutes and mechanically scored using a 1-ml glass pipette and subsequently transferred to non-adherent plates for culture overnight. During the pre-operative preparation of the mice, the cells were centrifuged in a 1.5 ml microfuge tube and most of the supernatant removed, leaving just enough to collect the pellet of cells. The cells were collected into a Rainin Pos-D positive displacement pipette and the pipette was inverted to allow for the cells to settle by gravity. The excess media was dispensed leaving a packed cell preparation for transplant.

For transplantation, a 24 G×¾" I.V. catheter was used to penetrate the kidney capsule and the needle was removed. The catheter was then advanced under the kidney capsule to the distal pole of the kidney. The Pos-D pipette tip was placed firmly in the hub of the catheter and the 5 million cells dispensed from the pipette through the catheter under the kidney capsule and delivered to the distal pole of the kidney. The kidney capsule was sealed with a low tempera-ture cautery and the kidney was returned its original ana-tomical position. In parallel, cell aggregates containing 5 million cells were loaded into the 50-μl device using Post-D pipette tip. The 50-1 devices were purchased from Thera-Cyte, Inc (Irvine, CA). The device was sealed by medical adhesive silicone type A (Dow Corning, Cat #129109) after the loading, and implanted subcutaneously into SICD/Bg mice (animal Nos. 3 and 4). The muscle was closed with continuous sutures using 5-0 vicryl and the skin closed with wound clips. Mice were dosed with 1.0 mg·kg Metacam subcutaneously post-operatively. The mouse was removed from the anesthesia and allowed to fully recover.

Following transplantation, mice were weighed once per week and blood glucose measured twice a week. At various intervals following transplantation, mice were dosed with 3 g/kg glucose IP and blood drawn via the retro-orbital sinus 60 minutes following glucose injection into microfuge tubes containing a small amount of heparin. The blood was centrifuged and the plasma placed into a second microfuge tube and frozen on dry ice and then stored at −80° C. until human c-peptide assay was performed. Human c-peptide levels were determined using the Mercodia/ALPCO Diag-nostics Ultrasensitive C-peptide ELISA (Cat No. 80-CPTHU-E01, Alpco Diagnostics, NH) according to the manufacturer's instructions.

Human C-peptide was detected in animal serum as early as 4 weeks after transplantation and increased over time. By the end of three months, the animals were fasted for about 15-20 hrs, after which a blood sample (pre-glucose) was withdrawn retro-orbitally. Each animal then received an intraperitoneal injection dose of about 3 g/kg of glucose in 30% dextrose solution, and blood was withdrawn at about 60 minutes post glucose infusion. The serum was separated from the blood cells through centrifugation in micro-containers. The ELISA analysis was performed on duplicated 25 μl of serum using an ultra-sensitive human specific C-peptide ELISA plates (Cat No. 80-CPTHU-E01, Alpco Diagnostics, NH). The detection of human C-peptide indicates that insulin secretion is derived from the grafted cells.

Figure 7B:
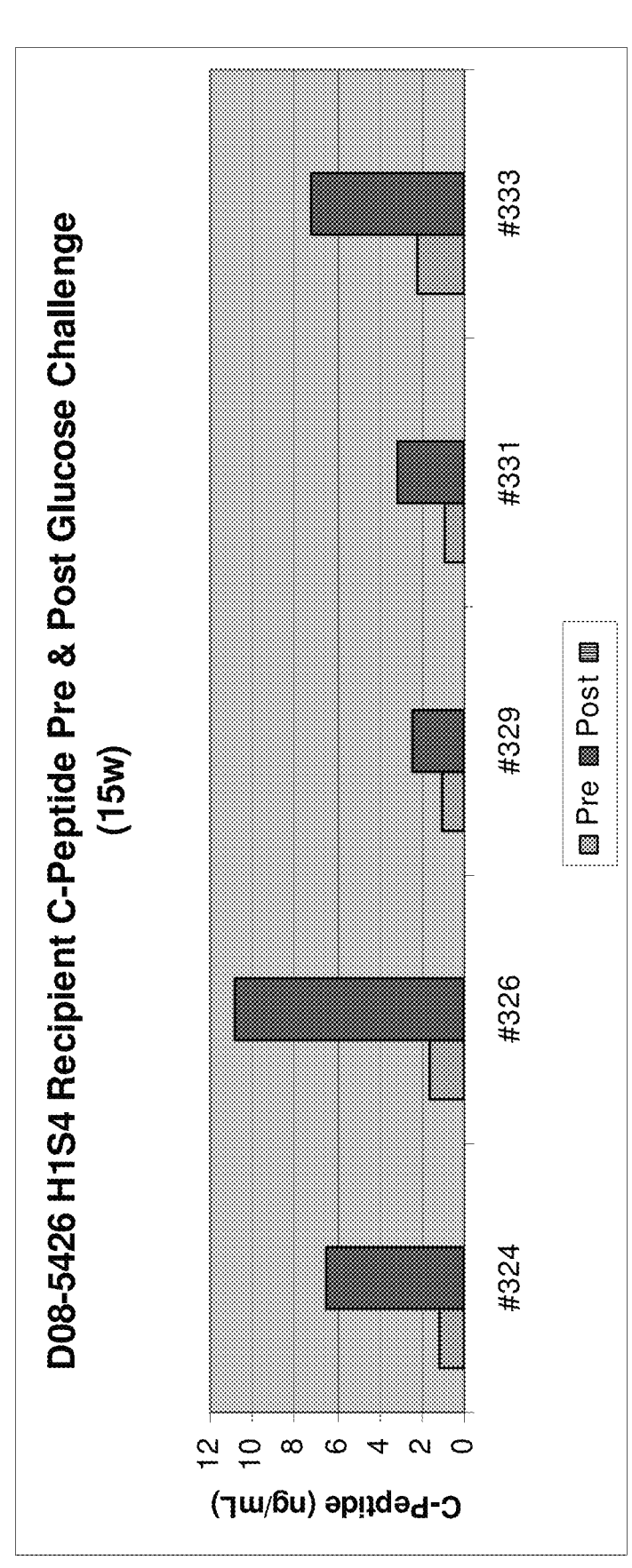
Figure 9B:
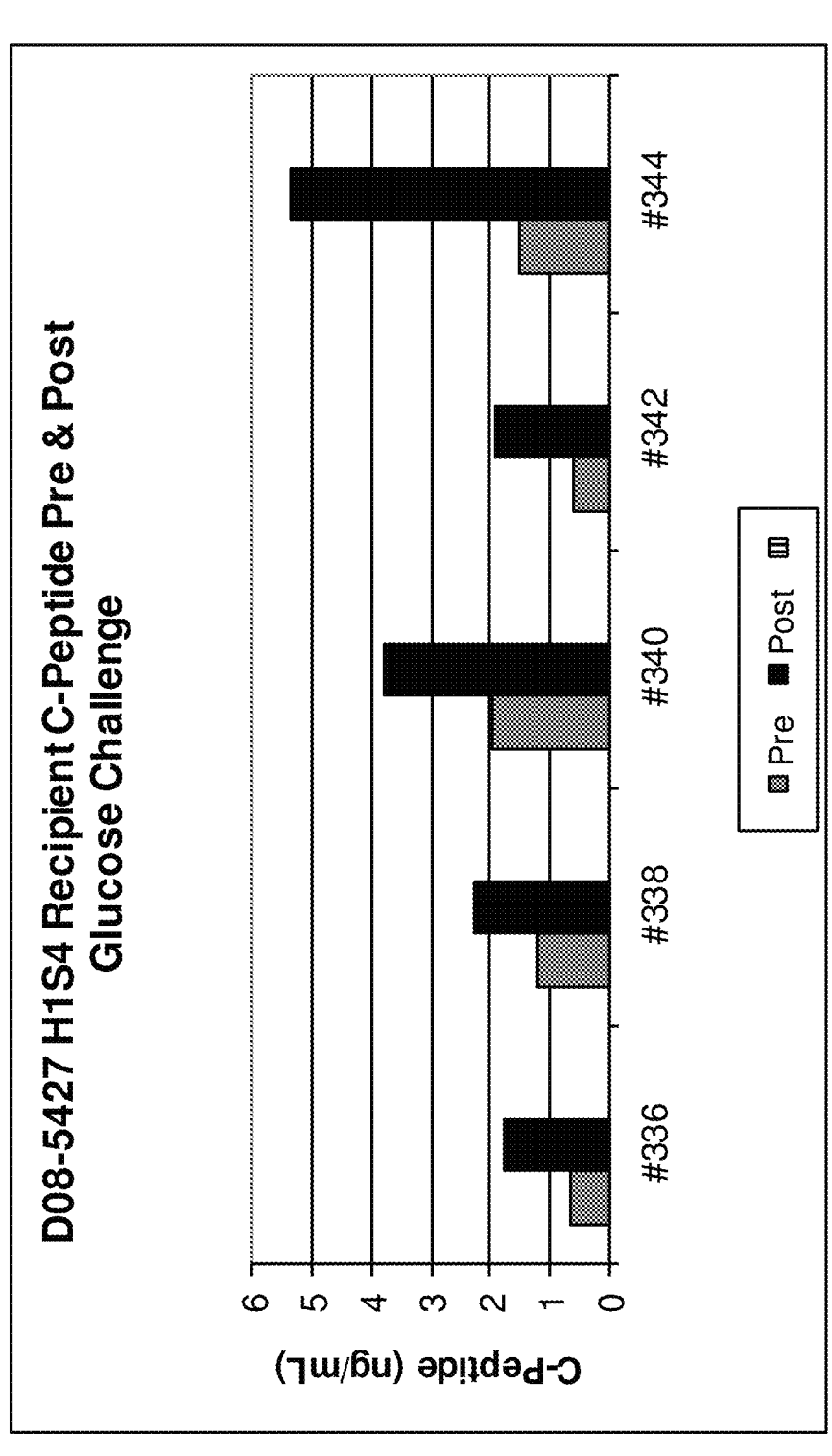
Figure 10B:
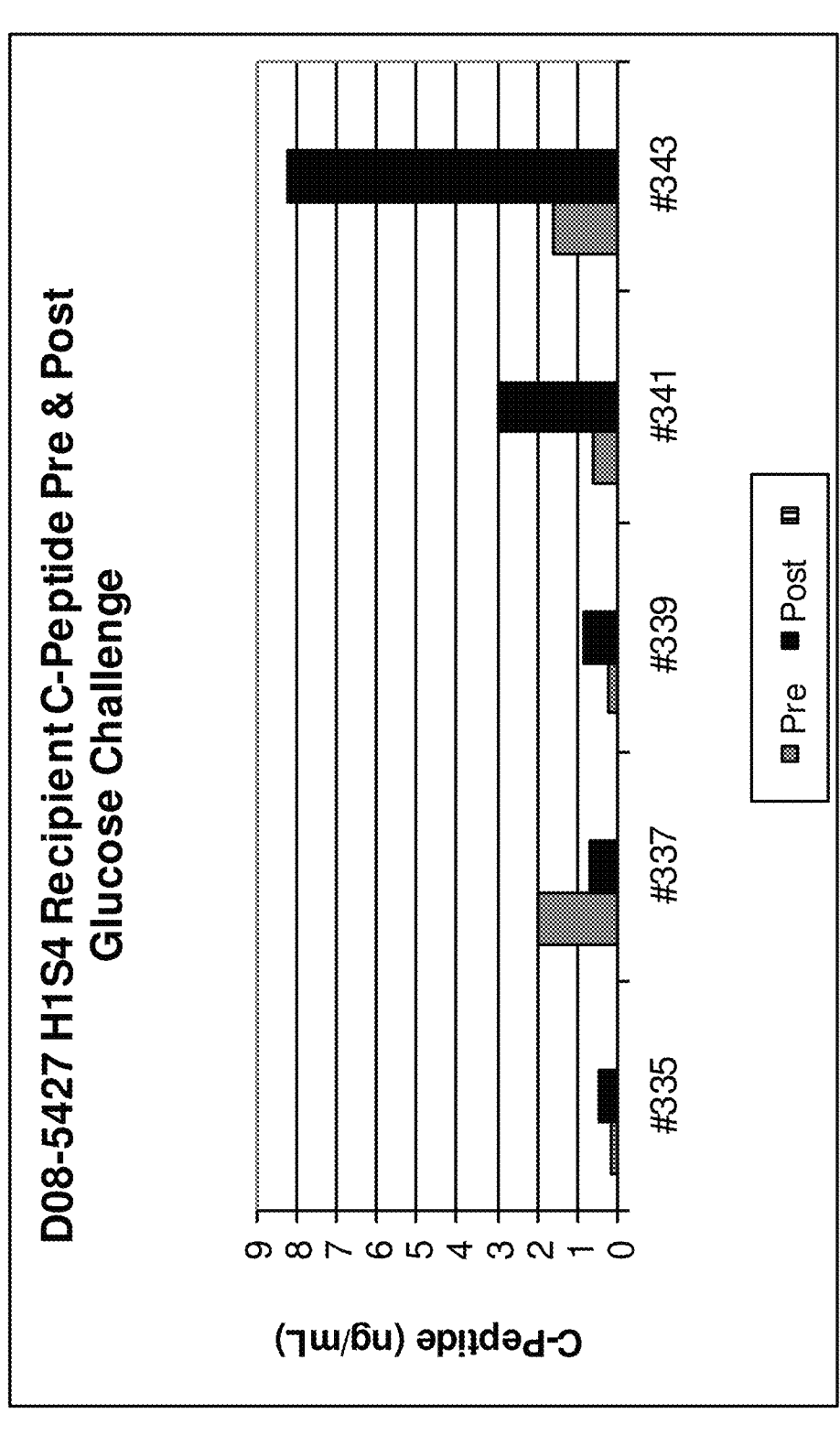

Low serum levels of human C-peptide (less than 0.5 ng/ml) were detected in response to glucose stimulation in all animals that received grafts containing pancreatic endocrine precursor cells, 60 days after transplantation. Between two to three months post-transplantation, glucose-stimulated human serum level increased rapidly in those animals (FIGS. 6-10). In general, those animals receiving cell cluster grafts also responded to glucose (FIGS. 7B, 9B and 10B).

Figure 11A:
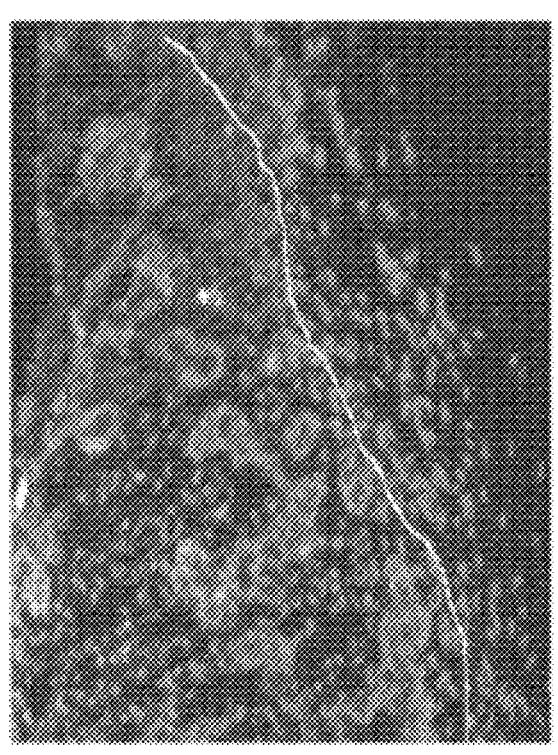
FIGS. 11A-11B shows the morphological and immunofluorescence analysis of graft samples 3 weeks post implant.
Figure 11B:

Histological examination of grafts harvested at different time points revealed the presence of human cells under the mice kidney capsule (as detected using human nuclear antigen staining). See FIGS. 11A-11B. Cells transplanted under the kidney capsule were observed to form duct-like structures three weeks after implantation. See FIG. 11A. The number of the duct-like structures increased with time. Most of the duct-like structures contained high levels of PDX1 and CK19 (FIG. 11B). This suggests that the pancreatic endocrine precursor cells were capable of differentiating further in vivo.

Since PDX1 expression in ducts is important for specifying progenitor populations that eventually form the endocrine pancreas, the co-expression of PDX1 with either insulin or glucagon in the grafts was determined. Insulin and glucagon expressing cells were observed in grafts as early as three weeks post-transplant (FIG. 12A). Most of endocrine hormonal expressing cells were formed when the PDX1 cells migrated out of the duct structure. A significant number of insulin positive cells were detected in the graft around 10-week time point; most of the insulin positive cells expressed PDX1 and NKX6.1 (FIG. 12B). These data correlate with the C-peptide expression date reported above. At 20 weeks, the number of insulin positive cells increased significantly, such that significant numbers of single cells, solely expressing insulin were detected in the graft. Most insulin expressing cells also expressed PDX1 (FIG. 12C), NKX6.1 (FIG. 12B), and NEUROD (FIG. 12E). PDX1 and NKX6.1 have been reported to be beneficial to the maintenance of glucose-stimulated insulin release of mature beta cells.

In a separate control experiment, animals received cells that were differentiated to the end of stage four in DMEM/F12, according to the methods described in Example 1. No human C-peptide was observed in the serum of any of the animals that received the cells, for up to three months post transplantation. Further, PCR and immunohistochemistry analysis did not reveal the expression of insulin, PDX1 or NKX6.1. However, a significant amount of glucagon positive cells were observed in the graft three month after transplantation.

Example 5

Histological Examination of Grafts

Histological examination of grafts harvested from animals receiving transplants were preformed substantially as described in previous example.

The grafts from the animals treated in the previous example, were dissected from the animals and washed with PBS−/− (not containing Mg++ and Ca++, Invitrogen) twice, and then transferred to 4% paraformaldehyde/PBS and fixed for about 2-3 hours at 4° C., and the PBS (−) was changed after 1 hour. The grafts were then equilibrated in 30% sucrose/PBS (−) overnight at 4° C. and mounted into OCT compound (SAKURA, #4583) and frozen with dry ice. The graft tissues were cut into 10 micron sections using a cryostat, and sections were stored at −80° C.

For analysis, the frozen sections were allowed to thaw to room temperature, and once thawed the sections were washed with PBS 2 times, in Shandon slide cassettes. The tissue sections were permeabilized with PBS+0.5% Triton-X for 20 minutes, followed by a 2 ml PBS wash. The sections were then incubated with a blocking solution containing 4% chicken serum/PBS. The slides were incubated for about 1 hour at room temperature. The blocking solution was removed away by 3 washes with 2 ml PBS. The sections were incubated again in the Shandon slide cassettes overnight at 4° C. with the primary antibodies, which were diluted in 4% chicken serum.

After incubation with the primary antibodies the sides were then washed with 2 ml PBS three times. The sections were again incubated in the Shandon slide cassettes at room temperature with the appropriate secondary antibodies, diluted in 4% chicken serum. After about 30 min to one hour, the sections were washed with 2 ml PBS 3 times before they were removed from the Shandon slide cassettes and mounted with Vectashield containing DAPI. Additional antibodies to other markers typical of pancreatic hormone secreting cells were analyzed including transcription factors PDX1. See Table 2 below.

TABLE 2

| Antibodies to pancreatic hormones and transcription factors | | | |
|---|---|---|---|
| Antibody | Host | Dilution | Provider |
| Insulin | Rabbit | 1:100 | Cell Signaling |
| PDX1 | Goat | 1:100 | Santa Cruz |
| Glucagon | Mouse | 1:100 | Sigma |
| CK19 | Mouse | 1:100 | Dako |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method for lowering blood glucose levels in a human, comprising transplanting a population of human pancreatic endocrine precursor cells expressing NKX6.1 and PDX1, but not expressing CDX2, into the liver, natural pancreas, renal subcapsular space, omentum, peritoneum, subserosal space, intestine, or a subcutaneous pocket of the mammal, wherein the pancreatic endocrine precursor cells express insulin and lower the blood glucose levels in the human.

2. The method of claim 1, wherein the population of pancreatic endocrine precursor cells further express one or more of NGN3, NeuroD, ISL1, PAX4, NKX2.2, and ARX.

3. The method of claim 1, wherein the population of pancreatic endocrine precursor cells are transplanted into the renal subcapsular space.

* * * * *